(12) United States Patent  
Walters et al.

(10) Patent No.: US 7,517,982 B2
(45) Date of Patent: Apr. 14, 2009

(54) NAPHTHOLS USEFUL FOR PREPARING INDENO-FUSED PHOTOCHROMIC NAPHTHOPYRANS

(75) Inventors: Robert W. Walters, County of Westmoreland, PA (US); Anil Kumar, County of Allegheny, PA (US); Clara E. Nelson, County of Allegheny, PA (US); Anu Chopra, County of Allegheny, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 11/712,657

(22) Filed: Mar. 1, 2007

(65) Prior Publication Data

US 2007/0155964 A1 Jul. 5, 2007

Related U.S. Application Data

(62) Division of application No. 10/393,177, filed on Mar. 20, 2003, now Pat. No. 7,262,295.

(51) Int. Cl.
C07D 265/30 (2006.01)
C07D 211/06 (2006.01)
(52) U.S. Cl. .................. 544/154; 546/195; 568/632; 568/713
(58) Field of Classification Search .................. None
See application file for complete search history.

(56) References Cited

U.S. PATENT DOCUMENTS

| | | | |
|---|---|---|---|
| 3,361,706 A | 1/1968 | Meriwether et al. | |
| 4,166,043 A | 8/1979 | Uhlmann et al. | |
| 4,360,653 A | 11/1982 | Stevens et al. | |
| 4,367,170 A | 1/1983 | Uhlmann et al. | |
| 4,556,605 A | 12/1985 | Mogami et al. | |
| 4,720,356 A | 1/1988 | Chu | |
| 4,756,973 A | 7/1988 | Sakagami et al. | |
| 4,798,745 A | 1/1989 | Martz et al. | |
| 4,798,746 A | 1/1989 | Claar et al. | |
| 4,873,029 A | 10/1989 | Blum | |
| 4,889,413 A | 12/1989 | Ormsby et al. | |
| 4,931,220 A | 6/1990 | Haynes et al. | |
| 4,994,208 A | 2/1991 | McBain et al. | |
| 5,166,345 A | 11/1992 | Akashi | |
| 5,200,483 A | 4/1993 | Selvig | |
| 5,236,958 A | 8/1993 | Miyashita | |
| 5,239,012 A | 8/1993 | McEntire et al. | |
| 5,252,742 A | 10/1993 | Miyashita | |
| 5,274,132 A | 12/1993 | VanGemert | |
| 5,359,085 A | 10/1994 | Iwamoto | |
| 5,373,033 A | 12/1994 | Toh et al. | |
| 5,391,327 A | 2/1995 | Ligas et al. | |
| 5,475,074 A | 12/1995 | Matsuoka et al. | |
| 5,488,119 A | 1/1996 | Fischer-Reimann et al. | |
| 5,618,586 A | 4/1997 | Swarup et al. | |
| 5,645,767 A | 7/1997 | Van Gemert | |
| 5,658,501 A | 8/1997 | Kumar et al. | |
| 5,753,146 A | 5/1998 | Van Gemert et al. | |
| 5,770,115 A | 6/1998 | Misura | |
| 5,821,287 A | 10/1998 | Hu et al. | |
| 5,869,658 A * | 2/1999 | Lin et al. | 544/106 |
| 5,936,016 A | 8/1999 | Lareginie et al. | |
| 5,961,631 A | 10/1999 | Devereux et al. | |
| 5,965,630 A | 10/1999 | Imafuku et al. | |
| 6,025,026 A | 2/2000 | Smith et al. | |
| 6,060,001 A | 5/2000 | Welch et al. | |
| 6,113,814 A | 9/2000 | Van Gemert et al. | |
| 6,146,554 A | 11/2000 | Melzig et al. | |
| 6,150,430 A | 11/2000 | Walters et al. | |
| 6,153,126 A | 11/2000 | Kumar | |
| 6,187,444 B1 | 2/2001 | Bowles, III et al. | |
| 6,225,466 B1 | 5/2001 | Mann et al. | |
| 6,268,055 B1 | 7/2001 | Walters et al. | |
| 6,296,785 B1 | 10/2001 | Nelson et al. | |
| 6,315,928 B1 | 11/2001 | Mann et al. | |
| 6,331,625 B1 | 12/2001 | Mann et al. | |
| 6,340,765 B1 | 1/2002 | Momoda et al. | |
| 6,348,604 B1 | 2/2002 | Nelson et al. | |
| 6,353,102 B1 | 3/2002 | Kumar | |
| 6,432,522 B1 | 8/2002 | Friedman et al. | |
| 6,432,544 B1 | 8/2002 | Stewart et al. | |
| 6,506,488 B1 | 1/2003 | Stewart et al. | |
| 6,555,028 B2 | 4/2003 | Walters et al. | |
| 6,683,709 B2 | 1/2004 | Mann et al. | |
| 7,166,357 B2 | 1/2007 | Kumar et al. | |
| 2004/0186241 A1 | 9/2004 | Gemert | |

FOREIGN PATENT DOCUMENTS

| | | |
|---|---|---|
| DE | 197 41 705 A1 | 4/1999 |
| EP | 1 054 010 A1 | 11/2000 |
| EP | 1 184 379 A1 | 6/2002 |
| WO | 96/14596 | 5/1996 |
| WO | 97/05213 | 2/1997 |
| WO | 01/19813 A1 | 3/2001 |
| WO | 01/94336 A1 | 12/2001 |

OTHER PUBLICATIONS

"Direct Substitution of Aromatic Ethers by Lithium Amides. A New Aromatic Amination Reaction" by Wolter ten Hoeve, et al., J. Orig. Chem. 1993, 58, 5101-5106.

Kirk-Othmer Encyclopedia of Chemical Technology, Fourth Edition, vol. 6, pp. 669-760.

Hawley's Condensed Chemical Dictionary, Thirteenth Edition, 1997, John Wiley & Sons, pp. 901-902.

(Continued)

*Primary Examiner*—Kamal A Saeed
(74) *Attorney, Agent, or Firm*—Frank P. Mallak; Deborah M. Altman

(57) ABSTRACT

Described are naphthols useful in the manufacture of novel indeno-fused photochromic naphthopyran materials.

3 Claims, No Drawings

OTHER PUBLICATIONS

*Friedel-Crafts and Related Reactions*, George A. Olah, Interscience Publishes, 1964, vol. 3, Chapter XXXI (Aromatic Ketone Synthesis).
Regioselective Friedel-Crafts Acylation of 1, 2, 3, 4-Tetrahydroquinoline and Related Nitrogen Heterocycles: Effect on NH Protective Groups and Rinig Size by Ishihara, Yugi et al., J. Chem. Soc., Perkin Trans. 1, pp. 3401 to 3406, 1992.
"*Organic Synthesis*", vol. 31, pp. 90-93, John Wiley & Sons, Inc., New York, New York.
Synthesis, Jan. 1995, pp. 41-43.
The Journal of Chemical Society Perkin Transaction I, 1995, pp. 235-241.
F.G. Baddar et al., The Journal of Chemical Society, p. 986, 1958.
*Techniques in Chemistry*, vol. III, "Photochromism", Chapter 3, Glenn H. Brown, Editor, John Wiley and Sons, Inc., New York, 1971.
*Ullmann's Encyclopedia of Industrial Chemistry*, Fifth Edition, 1992, vol. A21, pp. 665 to 716.

* cited by examiner

NAPHTHOLS USEFUL FOR PREPARING INDENO-FUSED PHOTOCHROMIC NAPHTHOPYRANS

CROSS-REFERENCE TO RELATED APPLICATIONS

This application is a division of U.S. patent application Ser. No. 10/393,177, filed Mar. 20, 2003 now U.S. Pat. No. 7,262,295.

BACKGROUND OF THE INVENTION

The present invention relates to novel naphthopyran materials. More particularly, this invention relates to indeno-fused photochromic naphthopyran materials and to compositions and articles comprising such naphthopyran materials. This invention also relates to naphthols used in making the novel naphthopyrans. When exposed to light radiation containing ultraviolet rays, such as the ultraviolet radiation in sunlight or the light of a mercury lamp, many photochromic materials exhibit a reversible change in color. When the ultraviolet radiation is discontinued, such a photochromic material will return to its original color or colorless state.

Various classes of photochromic materials have been synthesized and suggested for use in applications in which a sunlight-induced reversible color change is desired. Although indeno-fused photochromic naphthopyrans are known, it has unexpectedly been discovered that materials demonstrating a bathochromic shift in the visible lambda max and/or an increase in sensitivity, which is measured as a change in optical density over time, can be prepared.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The phrase "an at least partial coating" means an amount of coating covering from a portion to the complete surface of the substrate. The phrase "an at least partially cured coating" refers to a coating in which the curable or cross-linkable components are at least partially cured, crosslinked and/or reacted. In alternate non-limiting embodiments of the present invention, the degree of reacted components, can vary widely, e.g., from 5% to 100% of all the possible curable, crosslinkable and/or reactable components. The phrase "being substantially free of spiro-substituents at the 13-position" means that a spiro-substituent such as fluoren-9-ylidene, adamantylidene, bornylidene or cyclooctylidene, is not present at the 13-position.

The phrase "an at least partially abrasion resistant coating or film" refers to a coating or film that demonstrates a Bayer Abrasion Resistance Index of from at least 1.3 to 10.0 in ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the untreated surface. Put another way, the percent transmittance of the treated surface can range from a percentage greater than the untreated surface up to 99.9.

In one non-limiting embodiment of the present invention, there is provided indeno-fused photochromic naphthopyrans having a bathochromically shifted visible wavelength and/or improved sensitivity. These materials can be described as photochromic materials of indeno [2',3':3,4]naphtho[1,2-b] pyran structure, characterized in that they have a nitrogen or sulfur containing substituent at the 11-position ring atom, are substantially free of spiro-substituents at the 13-position and have been adapted to provide an increase in the sensitivity, visible lambda max or a combination thereof as measured in the Indenonaphthopyran Photochromic Performance Test described in Example 9 herein.

The ring atoms are numbered according to the International Union of Pure and Applied Chemistry rules of nomenclature starting with the 1-position ring atom being the carbon atom para to the oxygen atom of the pyran ring and numbering clockwise therefrom. In one non-limiting embodiment, the indeno [2',3':3,4]naphtho[1,2-b]pyran structure of the present invention has a nitrogen or sulfur containing substituent at the 11 position and is substantially free of substituents at the other available positions. In another non-limiting embodiment, various substituents can be located at the 3-position of the pyran ring. In a further non-limiting embodiment, other substituents can be present at the number 6, 7, 8, 9, 10, 12 and/or 13 carbon atoms of the materials.

In one non-limiting embodiment, the naphthopyran materials of the present invention can be represented by the following graphic formula I in which the letters a through n represent the sides of the naphthopyran rings, and the numbers represent the numbers of the ring atoms of the naphthopyran and in the definitions of the substituents, like symbols have the same meaning unless stated otherwise.

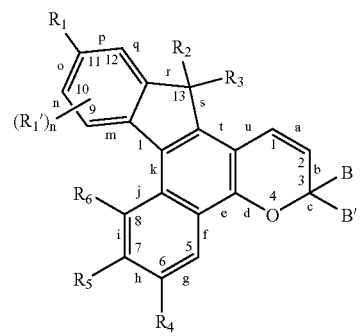

In alternate non-limiting embodiments, $R_1$ in graphic formula I is represented by:

(i) —$SR_7$, $R_7$ being chosen from $C_1$-$C_6$ alkyl, aryl, mono- or di-substituted aryl, said aryl group being phenyl or naphthyl and each of said aryl substitutents being chosen independently from $C_1$-$C_6$ alkyl, $C_1$-$C_6$ alkoxy or halogen;

(ii) —N($R_{15}$)$R_{16}$, $R_{15}$ and $R_{16}$ each being independently chosen from hydrogen, $C_1$-$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl and said aryl group being phenyl or naphthyl;

(iii) a nitrogen containing ring represented. by the following graphic formula IIA:

IIA

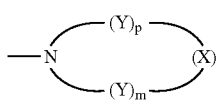

wherein each Y being independently chosen for each occurrence from —$CH_2$—, —CH($R_{17}$)—, —C($R_{17}$)($R_{17}$)—, —CH(aryl) -, —C(aryl)$_2$- or —C($R_{17}$)(aryl)-; X being —Y—, —O—, —S—, —S(O)—, —S(O$_2$)—, —NH—, —N($R_{17}$)— or —N(aryl)-; $R_{17}$ being $C_1$-$C_6$ alkyl; said aryl group being phenyl or naphthyl, m being chosen from the integer 1, 2 or 3 and p being chosen from the integer 0, 1, 2 or 3; provided that when p is 0, X is Y;

(iv) a group represented by one of the following graphic formulae IIB or IIC:

IIB

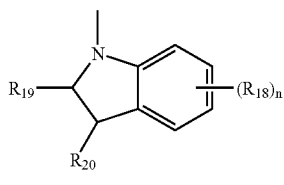

IIC

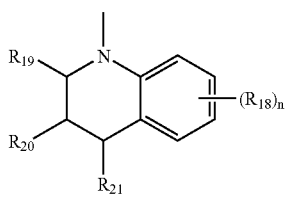

wherein each $R_{19}$, $R_{20}$ and $R_{21}$ being chosen independently for each occurrence in each formula from hydrogen, $C_1$-$C_5$ alkyl, phenyl or naphthyl; or the groups $R_{19}$ and $R_{20}$ together form a ring of 5 to 8 carbon atoms, for example, when $R_{19}$ and $R_{20}$ come together to form a ring of 6 carbon atoms on the group represented by graphic formula IIB, the resulting unsaturated group is carbazol-9-yl and the saturated group is tetrahydrocarbazol-9-yl, $R_{18}$ being chosen independently for each occurrence from $C_1$-$C_6$ alkyl, $C_{1-6}$ alkoxy, fluoro or chloro and n being chosen from the integer 0, 1 or 2;

(v) unsubstituted, mono- or di- substituted $C_4$-$C_{18}$ spirobicyclic amine; or (vi) unsubstituted, mono- or di- substituted $C_4$-$C_{18}$ spirotricyclic amine.

The substituents for (v) and (vi) are independently chosen for each occurrence from aryl, $C_1$-$C_6$ alkyl, $C_1$-$C_6$ alkoxy or phenyl ($C_1$-$C_6$)alkyl. Non-limiting examples of mono- or di-substituted bicyclicamines include: 2-azabicyclo[2.2.1] hept-2-yl; 3-azabicyclo[3.2.1]oct-3-yl; 2-azabicyclo[2.2.2] oct-2-yl; 6-azabicyclo[3.2.2]nonan-6-yl and tricyclicamines include: 6-azatricyclo[3.3.1.1(3,7)]decan-2-yl; 4-benzyl-2-azatricyclo[3.3.1.1(3,7)]decan-2-yl;4-methoxy-6-methyl-2-azatricyclo[3.3.1.1(3,7)]decan-2-yl;4-azatricyclo[4.3.1.1(3, 8)]undecan-4-yl; and 7-methyl-4-azatricyclo[4.3.1.1(3,8)] undecan-4-yl.

In one non-limiting embodiment, each $R_1'$ in graphic formula I is independently chosen for each occurrence from $C_1$-$C_6$ alkyl or $C_1$-$C_6$ alkoxy and n being chosen from the integer 0, 1 or 2.

$R_2$ and $R_3$ are each independently chosen from the following alternate non-limiting embodiments:

(i) hydrogen, hydroxy, amino, mono- or di-substituted amino, $C_1$-$C_{12}$ alkyl, $C_3$-$C_{12}$ alkylidene, $C_2$-$C_{12}$ alkylidyne, vinyl, $C_3$-$C_7$ cycloalkyl, $C_1$-$C_6$ haloalkyl, allyl, benzyl, mono-substituted benzyl, chloro, fluoro or the group, —C(O)W, wherein W being hydroxy, $C_1$-$C_6$ alkyl, $C_1$-$C_6$ alkoxy, phenyl, mono-substituted phenyl, amino, mono($C_1$-$C_6$)alkylamino, di($C_1$-$C_6$)alkylamino, morpholino, piperidino or pyrrolidyl; said amino substituents being $C_1$-$C_6$ alkyl, phenyl, benzyl or naphthyl; each of said benzyl and phenyl substituents being $C_1$-$C_6$ alkyl or $C_1$-$C_6$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (ii) being chosen independently for each occurrence from chloro, fluoro, $C_1$-$C_6$ alkyl or $C_1$-$C_6$ alkoxy;

(iii) a mono-substituted phenyl, said phenyl having a substituent located at the para position being a linking group, —(CH$_2$)$_t$— or —O—(CH$_2$)$_t$—, connected to an aryl group which is a member of another photochromic material, such as a naphthopyran or benzopyran, and t being chosen from the integer 1, 2, 3, 4, 5 or 6;

(iv) —OR$_8$, $R_8$ being chosen from $C_1$-$C_6$ alkyl, $C_1$-$C_6$ acyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, tri($C_1$-$C_6$)alkylsilyl, tri($C_1$-$C_6$)alkoxysilyl, di($C_1$-$C_6$) alkyl ($C_1$-$C_6$ alkoxy)silyl, di($C_1$-$C_6$)alkoxy($C_1$-$C_6$ alkyl)silyl, benzoyl, mono-substituted benzoyl, naphthoyl or mono-substituted naphthoyl; each of said benzoyl and naphthoyl substituents being independently chosen from $C_1$-$C_6$ alkyl or $C_1$-$C_6$ alkoxy; or $R_8$ being —CH($R_9$)Q, wherein $R_9$ being chosen from hydrogen or $C_1$-$C_3$ alkyl and Q being chosen from —CN, —CF$_3$, or —COOR$_{10}$ and $R_{10}$ being chosen from hydrogen or $C_1$-$C_3$ alkyl; or $R_8$ being —C(O)V, wherein V being chosen from hydrogen, $C_1$-$C_6$ alkoxy, phenoxy, mono- or di-($C_1$-$C_6$)alkyl substituted phenoxy, mono- or di-($C_1$-$C_6$)alkoxy substituted phenoxy, an unsubstituted, mono- or di-substituted aryl group, phenyl or naphthyl, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; each of said aryl group substituents being independently chosen from $C_1$-$C_6$ alkyl or $C_1$-$C_6$ alkoxy;

(v) —CH(Q')$_2$, Q' being chosen from —CN or —COOR$_{11}$ and $R_{11}$ being chosen from hydrogen, $C_1$-$C_6$ alkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl ($C_1$-$C_3$)alkyl or an unsubstituted, mono- or di-substituted aryl group, phenyl or naphthyl; each of said aryl group substituents being independently chosen from $C_1$-$C_6$ alkyl or $C_1$-$C_6$ alkoxy;

(vi) —CH($R_{12}$)G, $R_{12}$ being chosen from hydrogen, $C_1$-$C_6$ alkyl or an unsubstituted, mono- or di-substituted aryl group, phenyl or naphthyl, and G being chosen from —COOR$_{11}$, —COR$_{13}$ or —CH$_2$OR$_{14}$, wherein $R_{13}$ being chosen from hydrogen, $C_1$-$C_6$ alkyl, an unsubstituted, mono- or di-substituted aryl group, phenyl or naphthyl, amino, mono($C_1$-$C_6$)alkylamino, di($C_1$-$C_6$) alkylamino, e.g., dimethyl amino, methyl propyl amino, etc., phenylamino, mono- or di-($C_1$-$C_6$)alkyl substituted phenylamino, e.g., each phenyl has one or two $C_1$-$C_6$ alkyl substituents, mono- or di-($C_1$-$C_6$)alkoxy substituted phenylamino, diphenylamino, mono- or di($C_1$-$C_6$) alkyl substituted diphenylamino, mono- or di($C_1$-$C_6$) alkoxy substituted diphenylamino, morpholino or piperidino $R_{14}$ being chosen from hydrogen, —C(O) $R_{11}$, $C_1$-$C_6$ alkyl, $C_1$-$C_3$ alkoxy($C_1$-$C_6$)alkyl, phenyl($C_1$-$C_3$)alkyl, mono($C_1$-$C_6$)alkoxy substituted phenyl($C_1$-$C_3$)alkyl or an unsubstituted, mono- or di-substituted aryl group, phenyl or naphthyl, each of said aryl group substituents being independently chosen from $C_1$-$C_6$ alkyl or $C_1$-$C_6$ alkoxy; or (vii) the group T represented by the formula:

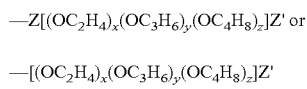

—Z[(OC$_2$H$_4$)$_x$(OC$_3$H$_6$)$_y$(OC$_4$H$_8$)$_z$]Z' or

—[(OC$_2$H$_4$)$_x$(OC$_3$H$_6$)$_y$(OC$_4$H$_8$)$_z$]Z' wherein -Z being chosen from —C(O)— or —CH$_2$—, Z' being chosen from $C_1$-$C_3$ alkoxy or a polymerizable group, defined herein as any functional group capable of participating in a polymerization reaction.

In one non-limiting embodiment, polymerization of the photochromic polymerizable materials can occur by mechanisms described in the definition of "polymerization" in *Hawley's Condensed Chemical Dictionary* Thirteenth Edition, 1997, John Wiley & Sons, pages 901-902, which disclosure is incorporated herein by reference. Those mechanisms include by "addition", in which free radicals are the initiating agents that react with the double bond of the monomer by adding to it on one side at the same time producing a new free electron on the other side, by "condensation", involving the splitting out of water molecules by two reacting monomers and by so-called "oxidative coupling".

Non-limiting examples of the polymerizable groups are hydroxy, (meth)acryloxy, 2-(methacryloxy)ethylcarbamyl, or epoxy, e.g., oxiranylmethyl. When there are 2 or more polymerizable groups on the naphthopyran, they may be the same or different.

In alternate non-limiting embodiments, the group, —(OC$_2$H$_4$)$_x$—, in the group T formulae, can represent poly (ethylene oxide); —(OC$_3$H$_6$)$_y$—, can represent poly(propylene oxide); and, —(OC$_4$H$_8$)$_z$—, can represent poly(butylene oxide). When used in combination, the poly(ethylene oxide), poly(propylene oxide) and poly(butylene oxide) groups of T can be in a random or block order within the T moiety. The letters x, y and z are each a number between 0 and 50 and the sum of x, y and z is between 2 and 50. The sum of x, y and z can be any number that falls within the range of 2 to 50, e.g., 2, 3, 4 . . . 50. This sum can also range from any lower number to any higher number within the range of 2 to 50, e.g., 6 to 50, 31 to 50. The numbers for x, y, and z are average values and can be partial numbers, e.g., 9.5.

In a further non-limiting embodiment, $R_2$ and $R_3$ can come together to form an oxo group.

$R_4$ in graphic formula I, in one non-limiting embodiment, is chosen from hydrogen, $C_1$-$C_6$ alkyl or the group $R_a$ chosen from:

(i) —OR$_8$', $R_8$' being chosen from phenyl($C_1$-$C_3$)alkyl, $C_1$-$C_6$ alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl or —CH(R$_9$)Q, $R_9$ being chosen from hydrogen or $C_1$-$C_3$ alkyl; or (ii) a group chosen from:
(1) —N(R$_{15}$)R$_{16}$ wherein $R_{15}$ and $R_{16}$ being the same as described hereinbefore for $R_1$;
(2) a nitrogen containing ring represented by graphic formula IIA wherein Y, X, m and p being the same as described hereinbefore for $R_1$; or
(3) a group represented by graphic formulae IIB or IIC wherein $R_{18}$, $R_{19}$, $R_{20}$, $R_{21}$ and n being the same as described hereinbefore for $R_1$.

$R_5$ and $R_6$ are each chosen independently in one non-limiting embodiment from hydrogen, $C_1$-$C_6$ alkyl or $R_a$, said $R_a$ being the same as described hereinbefore for $R_4$. In an alternate non-limiting embodiment, $R_5$ and $R_6$ can come together to form one of the following graphic formulae IID or IIE:

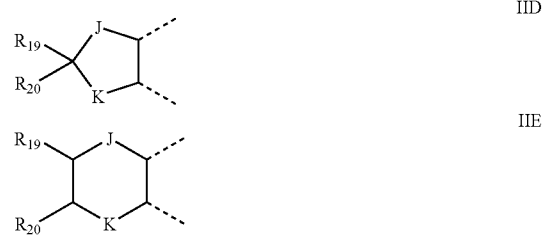

wherein J and K being independently chosen for each occurrence in each formula from oxygen or —N(R$_{15}$)—, $R_{15}$, $R_{19}$ and $R_{20}$ each being the same as described hereinbefore for $R_1$.

B and B' in graphic formula I, in one non-limiting embodiment, are each independently chosen from:

(i) mono-T-substituted phenyl, the group T being the same as described hereinbefore for $R_2$ and $R_3$;
(ii) an unsubstituted, mono-, di-, or tri-substituted aryl group, phenyl or naphthyl;
(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (ii) and (iii) being independently chosen from hydroxy, the group, —C(O)W, defined hereinbefore for $R_2$ and $R_3$, aryl, mono($C_1$-$C_6$)alkoxyaryl, di($C_1$-$C_6$)alkoxyaryl, mono ($C_1$-$C_6$)alkylaryl, di($C_1$-$C_6$)alkylaryl, chloroaryl, fluoroaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_6$)alkyl, $C_3$-$C_7$ cycloalkyloxy($C_1$-$C_6$)alkoxy, aryl($C_1$-$C_6$)alkyl, aryl($C_1$-$C_6$)alkoxy, aryloxy, aryloxy($C_1$-$C_6$)alkyl, aryloxy($C_1$-$C_6$)alkoxy, mono- or di-($C_1$-$C_6$)alkylaryl($C_1$-$C_6$)alkyl, mono- or di-($C_1$-$C_6$)alkoxyaryl($C_1$-$C_6$)alkyl, mono- or di-($C_1$-$C_6$)alkylaryl($C_1$-$C_6$)alkoxy, mono- or di-($C_1$-$C_6$)alkoxyaryl($C_1$-$C_6$)alkoxy, amino, mono($C_1$-$C_6$)alkylamino, di($C_1$-$C_6$)alkylamino, diarylamino, piperazino, N—($C_1$-$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_6$ alkyl, $C_1$-$C_6$ chloroalkyl, $C_1$-$C_6$ fluoroalkyl, $C_1$-$C_6$ alkoxy, mono($C_1$-$C_6$)alkoxy($C_1$-$C_4$) alkyl, acryloxy, methacryloxy, bromo, chloro or fluoro, said aryl being chosen from phenyl or naphthyl;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$-$C_6$ alkyl, $C_1$-$C_6$ alkoxy, phenyl, fluoro, chloro or bromo;

(v) a monosubstituted phenyl, said phenyl having a substituent located at the para position being a linking group, —$(CH_2)_t$— or —O—$(CH_2)_t$—, connected to an aryl group which is a member of another photochromic material, such as a naphthopyran or benzopyran, and t being chosen from the integer 1, 2, 3, 4, 5 or 6;

(vi) a group represented by one of the following graphic formulae IIF or IIG:

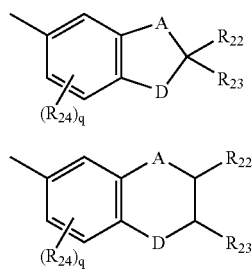

IIF

IIG wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$-$C_6$ alkyl, or $C_2$-$C_6$ acyl; each $R_{24}$ being independently chosen for each occurrence in each formula from $C_1$-$C_6$ alkyl, $C_1$-$C_6$ alkoxy, hydroxy, chloro or fluoro; $R_{22}$ and $R_{23}$ each being independently chosen in each formula from hydrogen or $C_1$-$C_6$ alkyl; and q being chosen from the integer 0, 1 or 2;

(vii) $C_1$-$C_6$ alkyl, $C_1$-$C_6$ chloroalkyl, $C_1$-$C_6$ fluoroalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)cycloalkyl, mono($C_1$-$C_6$)alkyl($C_3$-$C_6$)cycloalkyl, chloro($C_3$-$C_6$)cycloalkyl, fluoro($C_3$-$C_6$) cyclo-alkyl or $C_4$-$C_{12}$ bicycloalkyl; or (viii) a group represented by the following graphic formula IIH:

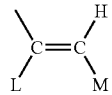

IIH wherein L being chosen from hydrogen or $C_1$-$C_4$ alkyl and M being chosen from an unsubstituted, mono-, or di-substituted group chosen from naphthyl, phenyl, furanyl, or thienyl; each of said group substituents being independently chosen from $C_1$-$C_4$ alkyl, $C_1$-$C_4$ alkoxy, fluoro, or chloro.

Alternatively, B and B' can together, in one nonlimiting embodiment, form fluoren-9-ylidene, mono-, or di-substituted fluoren-9-ylidene or a group being independently chosen from saturated $C_3$-$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene or cyclododecylidene, saturated $C_7$-$C_{12}$ spiro-bicyclic hydrocarbon rings, e.g., bicyclo[2.2.]heptylidene, i.e., norbornylidene, 1,7,7-trimethyl bicyclo[2.2.]heptylidene, i.e., bornylidene, bicyclo[3.2.]octylidene, bicyclo[3.3.1]nonan-9-ylidene or bicyclo[4.3.2]undecane, or saturated $C_7$-$C_{12}$ spiro-tricyclic hydrocarbon rings, e.g., tricyclo[2.2.1.0$^{2,6}$] heptylidene, tricyclo[3.3.1.1$^{3,7}$]decylidene, i.e., adamantylidene, and tricyclo[5.3.1.1$^{2,6}$]dodecylidene; each of said fluoren-9-ylidene substituents being independently chosen from $C_1$-$C_4$ alkyl, $C_1$-$C_4$ alkoxy, fluoro or chloro.

In alternate non-limiting embodiments, the substituents of the naphthopyran of the present invention can be chosen from the following:

(a) $R_1$ being represented by:
(i) —$SR_7$, $R_7$ being chosen from $C_1$-$C_6$ alkyl or aryl, said aryl group being phenyl;
(ii) —$N(R_{15})R_{16}$, $R_{15}$ and $R_{16}$ each being independently chosen from hydrogen, $C_1$-$C_6$ alkyl, phenyl or $C_3$-$C_{20}$ cycloalkyl;
(iii) a nitrogen containing ring represented by the graphic formula IIA wherein each Y being —$CH_2$— and X being independently chosen from —Y—, —O—, —S—, —N($R_{17}$)— and —N(phenyl)-, $R_{17}$ being $C_1$-$C_6$ alkyl, m being chosen from the integer 1, 2 or 3, and p being chosen from the integer 0, 1, 2 or 3;
(iv) a group represented by one of graphic formulae IIB or IIC wherein $R_{19}$, $R_{20}$ and $R_{21}$ each being independently chosen from hydrogen or $C_1$-$C_5$ alkyl, $R_{18}$ being independently chosen from hydrogen, $C_1$-$C_4$ alkyl, $C_1$-$C_4$ alkoxy, fluoro or chloro and n being chosen from the integer 0 or 1;
(v) unsubstituted or mono-substituted $C_5$-$C_{18}$ spirobicyclic amine; or
(vi) unsubstituted or mono-substituted $C_5$-$C_{18}$ spirotricyclic amine;

(b) $R_1'$ being independently chosen from $C_1$-$C_4$ alkyl or $C_1$-$C_4$ alkoxy and n being chosen from the integer 0 or 1;

(c) $R_2$ and $R_3$ each being independently chosen from:
(i) hydrogen, hydroxy, $C_3$-$C_7$ cycloalkyl, allyl, benzyl or the group, —C(O)W, wherein W being $C_1$-$C_6$ alkyl or $C_1$-$C_6$ alkoxy;
(ii) an unsubstituted or mono-substituted phenyl, said substituent being chosen from chloro, fluoro, $C_1$-$C_4$ alkyl or $C_1$-$C_4$ alkoxy;
(iii) a monosubstituted phenyl, having a substituent at the para position that is a linking group chosen from —$(CH_2)_t$— or —O—$(CH_2)_t$—, wherein t being chosen from the integer 2 or 3, connected to an aryl group which is a member of another photochromic naphthopyran;
(iv) —$OR_8$, $R_8$ being chosen from $C_1$-$C_6$ alkyl, $C_1$-$C_6$ acyl or phenyl($C_1$-$C_3$)alkyl; or $R_8$ being the group —CH($R_9$) Q, wherein $R_9$ being hydrogen and Q being —$COOR_{10}$, $R_{10}$ being $C_1$-$C_3$ alkyl, or $R_8$ being the group, —C(O)V, wherein V being $C_1$-$C_6$ alkoxy;
(v) —$CH(Q')_2$, $Q'$ being —$COOR_{11}$, wherein $R_{11}$ being $C_1$-$C_6$ alkyl;
(vi) —$CH(R_{12})G$, $R_{12}$ being hydrogen or $C_1$-$C_6$ alkyl; G being —$COOR_{11}$ or —$CH_2OR_{14}$, wherein $R_{14}$ being hydrogen, $C_1$-$C_6$ alkyl, or $C_1$-$C_3$ alkoxy($C_1$-$C_6$)alkyl;

(vii) the group T represented by the formula:

wherein -Z being —CH$_2$—, Z' being C$_1$-C$_3$ alkoxy or a polymerizable group, x, y and z each being independently chosen from a number between 0 and 30, and the sum of x, y and z being between 2 and 30; or (viii) R$_2$ and R$_3$ together form an oxo group;

(d) R$_4$ being hydrogen, C$_1$-C$_6$ alkyl or R$_a$, said R$_a$ being chosen from:

(i) —OR$_8$', R$_8$' being phenyl(C$_1$-C$_3$)alkyl or C$_1$-C$_6$ alkyl; or (ii) —N(R$_{15}$)R$_{16}$, R$_{15}$ and R$_{16}$ each being independently chosen from hydrogen, C$_1$-C$_6$ alkyl, phenyl or C$_3$-C$_{20}$ cycloalkyl;

(iii) a nitrogen containing ring represented by graphic formula IIA wherein each Y being —CH$_2$—, and X being independently chosen from —Y—, —O—, —S—, —NH—, —N(R$_{17}$)— or —N(aryl)-, wherein R$_{17}$ is C$_1$-C$_6$ alkyl, said aryl being chosen from phenyl or naphthyl, m being chosen from the integer 1, 2 or 3, and p being chosen from the integer 0, 1, 2 or 3 provided that when p is 0, X is Y; or (iv) a group represented by one of graphic formulae IIB or IIC wherein R$_{19}$, R$_{20}$ and R$_{21}$ each being independently chosen from hydrogen, C$_1$-C$_5$ alkyl or phenyl;

(e) R$_5$ being chosen from hydrogen, C$_1$-C$_4$ alkyl or R$_a$, said R$_a$ being described hereinbefore in (d);

(f) R$_6$ being chosen from hydrogen, C$_1$-C$_4$ alkyl or R$_a$, said R$_a$ being described hereinbefore in (d); or (g) R$_5$ and R$_6$ together form one of graphic formula IID or IIE wherein J and K each being oxygen; and R$_{19}$ and R$_{20}$ being the same as described hereinbefore in (d)(iv);

(h) B and B' each being independently chosen from:

(i) mono-T-substituted phenyl;

(ii) an unsubstituted, mono-, di-, or tri-substituted aryl group, said aryl being phenyl or naphthyl;

(iii) 9-julolidinyl or the unsubstituted, mono-or di-substituted heteroaromatic group chosen from pyridyl, benzofuran-2-yl, benzofuran-3-yl, thienyl, benzothien-2-yl, benzothien-3-yl, dibenzofuranyl, dibenzothienyl, or carbazoyl, each of said aryl and heteroaromatic substituents in (h) (ii) and (iii) being independently chosen from hydroxy, C$_3$-C$_7$ cycloalkyl, C$_3$-C$_7$ cycloalkyloxy, aryl (C$_1$-C$_6$)alkyl, aryloxy, aryloxy(C$_1$-C$_6$)alkoxy, amino, mono(C$_1$-C$_6$)alkylamino, di(C$_1$-C$_6$)alkylamino, diarylamino, piperazino, N-arylpiperazino, indolino, piperidino, morpholino, thiomorpholino, pyrrolidyl, C$_1$-C$_6$ alkyl, C$_1$-C$_6$ alkoxy or fluoro;

(iv) an unsubstituted or mono-substituted group chosen from phenothiazinyl or phenoxazinyl, each of said substituents being independently chosen from C$_1$-C$_6$ alkyl or C$_1$-C$_6$ alkoxy;

(v) a monosubstituted phenyl, said phenyl having a substituent at the para position as described hereinbefore in (c)(iii);

(vi) a group represented by one of graphic formulae IIF or IIG wherein A being independently chosen in each formula from methylene or oxygen and D being independently chosen in each formula from oxygen or substituted nitrogen, provided that when D is substituted nitrogen, A is methylene, said nitrogen substituents being chosen from hydrogen or C$_1$-C$_4$ alkyl; each R$_{24}$ being C$_1$-C$_4$ alkyl; R$_{22}$ and R$_{23}$ each being hydrogen; and q being the integer 0, 1 or 2;

(vii) C$_1$-C$_6$ alkyl, C$_3$-C$_6$ cycloalkyl or C$_4$-C$_{12}$ bicycloalkyl;

(viii) a group represented by graphic formula IIH wherein L being chosen from hydrogen or C$_1$-C$_4$ alkyl and M being chosen from an unsubstituted, mono-, or di-substituted phenyl; each of said phenyl substituents being independently chosen from C$_1$-C$_4$ alkyl or C$_1$-C$_4$ alkoxy; or (i) B and B' taken together form fluoren-9-ylidene or mono-substituted fluoren-9-ylidene or a group being independently chosen from saturated C$_3$-C$_{12}$ spiro-monocyclic hydrocarbon rings, saturated C$_7$-C$_{12}$ spiro-bicyclic hydrocarbon rings or saturated C$_7$-C$_{12}$ spiro-tricyclic hydrocarbon rings; said fluoren-9-ylidene substituent being chosen from C$_1$-C$_4$ alkyl or C$_1$-C$_4$ alkoxy.

In further alternate non-limiting embodiments, the substituents of the naphthopyran can be chosen from:

(a) R$_1$ being represented by:

(i) —N(R$_{15}$)R$_{16}$, R$_{15}$ and R$_{16}$ each being independently chosen from C$_1$-C$_4$ alkyl or phenyl;

(ii) a nitrogen containing ring represented by graphic formula IIA wherein each Y for each occurrence being —CH$_2$— and X being independently chosen from —Y—, —O—, and —N(R$_{17}$)—, R$_{17}$ being C$_1$-C$_4$ alkyl, m being chosen from the integer 1 or 2, and p being chosen from the integer 0, 1 or 2; or (iii) a group represented by graphic formulae IIC or IIB wherein R$_{19}$, R$_{20}$, and R$_{21}$ each being hydrogen and n is 0;

(b) R$_1$, being C$_1$-C$_2$ alkyl or C$_1$-C$_3$ alkoxy;

(c) R$_2$ and R$_3$ each being independently chosen from:

(i) hydrogen, hydroxy or C$_3$-C$_7$ cycloalkyl;

(ii) phenyl or mono-(C$_1$-C$_4$ alkoxy) substituted phenyl;

(iii) a monosubstituted phenyl, having a substituent at the para position being a linking group, —O—(CH$_2$)$_t$—, t being chosen from the integer 2 or 3, connected to an aryl group being a member of another photochromic naphthopyran;

(iv) —OR$_8$, R$_8$ being C$_1$-C$_6$ alkyl or —CH(R$_9$)Q, R$_9$ being hydrogen, Q being —COOR$_{10}$ and R$_{10}$ being C$_1$-C$_3$ alkyl;

(v) —CH(R$_{12}$)G, R$_{12}$ being hydrogen; G being —COOR$_{11}$, wherein R$_{10}$ being C$_1$-C$_6$ alkyl or C$_1$-C$_3$ alkoxy(C$_1$-C$_6$)alkyl; or (vi) the group T represented by the formula:

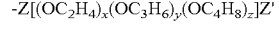

wherein -Z being —CH$_2$—, Z' being C$_1$-C$_3$ alkoxy, x, y and z each being independently chosen from a number between 0 and 20, and the sum of x, y and z being between 2 and 20;

(d) R$_4$ being hydrogen, C$_1$-C$_6$ alkyl or R$_a$, said R$_a$ being chosen from:

(i) —OR$_8$', R$_8$' being C$_1$-C$_4$ alkyl;

(ii) —N(R$_{15}$)R$_{16}$, R$_{15}$ and R$_{16}$ each being independently chosen from C$_1$-C$_4$ alkyl or phenyl; or (iii) a nitrogen containing ring represented by graphic formula IIA wherein each Y being —CH$_2$—, and X being independently chosen from —Y—, —O—, —S—, and —N(R$_{17}$)—, R$_{17}$ being C$_1$-C$_4$ alkyl, m being chosen form the integer 1, 2 or 3, and p being chosen form the integer 0, 1, 2 or 3;

(e) R$_5$ being hydrogen or C$_1$-C$_4$ alkyl;

(f) R$_6$ being hydrogen;

(g) B and B' each being independently chosen from:

(i) mono-, di-, and tri-substituted phenyl;

(ii) an unsubstituted, mono- or di-substituted heteroaromatic group chosen from benzofuran-2-yl or dibenzofuranyl, each of said aryl and heteroaromatic substituents in (g) (i) and (ii) being independently chosen from $C_3$-$C_7$ cycloalkyl, aryloxy, aryloxy($C_1$-$C_6$)alkoxy, di($C_1$-$C_6$)alkylamino, piperazino, indolino, piperidino, morpholino, pyrrolidyl, $C_1$-$C_6$ alkyl, $C_1$-$C_6$ alkoxy or fluoro;
(iii) a monosubstituted phenyl, said phenyl having a substituent at the para position as described hereinbefore in (c)(iii);
(iv) a group represented by one of the following graphic formulae:

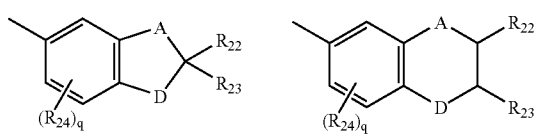

wherein A being methylene and D being independently chosen in each formula from oxygen or substituted nitrogen, said nitrogen substituents being $C_1$-$C_3$ alkyl; each $R_{24}$ being $C_1$-$C_3$ alkyl; $R_{22}$ and $R_{23}$ each being hydrogen; and q being chosen from the integer 0, 1 or 2;
(v) $C_1$-$C_4$ alkyl or $C_3$-$C_5$ cycloalkyl;
(vi) the group represented by graphic formula IIH wherein L being hydrogen and M being chosen from an unsubstituted, mono-, or di-substituted phenyl, each of said phenyl substituents being $C_1$-$C_4$ alkoxy; or
(i) B and B' taken together form fluoren-9-ylidene, monosubstituted fluoren-9-ylidene or a saturated $C_7$-$C_{12}$ spiro-bicyclic hydrocarbon rings, each of said fluoren-9-ylidene substituents being $C_1$-$C_4$ alkoxy.

Materials represented by graphic formula I having substituents $R_1$-$R_6$, $R_1'$, B and B' described hereinbefore, can be prepared by the methods of the following Reactions A through H. Additional methods for preparing materials of graphic formula I having substituents $R_2$-$R_6$, $R_1'$, B and B' are disclosed in U.S. Pat. No. 6,296,785B1 column 10, line 52 to column 29, line 18, which disclosure is incorporated herein by reference.

With reference to the following reactions, compounds represented by graphic formula V, VA, or VB are prepared by methods known to those skilled in the art, for example, by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

By way of non-limiting illustration in Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B or VB in Reaction C). R and R' represent possible substituents, as described hereinbefore with respect to B and B' of graphic formula I.

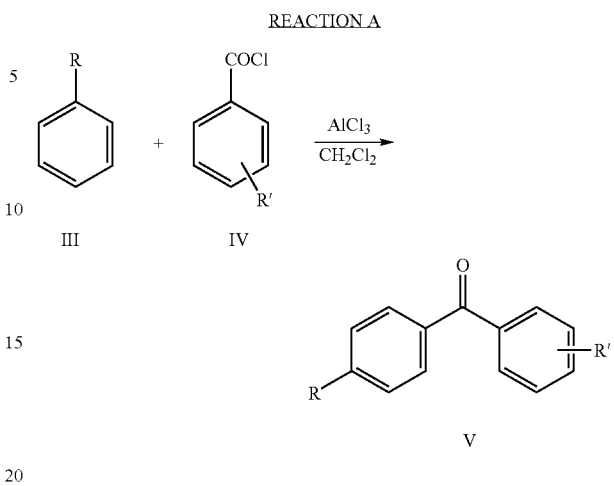

Further by way of non-limiting illustration in Reaction B, the substituted or unsubstituted ketone represented by graphic formula VA, in which B and B' can represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl can, for example, be prepared from commercially available ketones or ketones prepared via reaction of an acyl halide with a substituted or unsubstituted benzene, naphthalene or heteroaromatic compound, e.g., 9-julolidinyl. Propargyl alcohols having a B or B' group represented by graphic formula IIH can be produced by methods known to those skilled in the art, for example, as described in U.S. Pat. No. 5,274,132, column 2, lines 40 to 68.

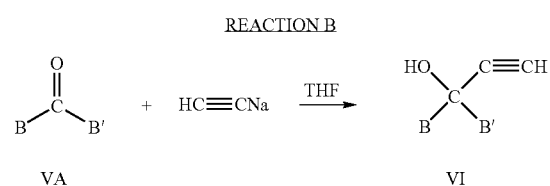

Further by way of non-limiting illustration in Reaction C, a substituted benzophenone represented by graphic formula VB having $SR_7$ as the $R_1$ substituent is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. A mixture of cis and trans half esters forms, which then undergoes cyclodehydration in the presence of acetic anhydride to form a mixture of acetoxynaphthalenes. Further purification to isolate the distinct isomer represented by graphic formula IX may be desirable. This product is hydrolyzed in an aqueous alcoholic solution of base, such as sodium hydroxide, followed by treatment with aqueous hydrochloric acid ($H^+$) to form the carboxynaphthol represented by graphic formula X.

REACTION C

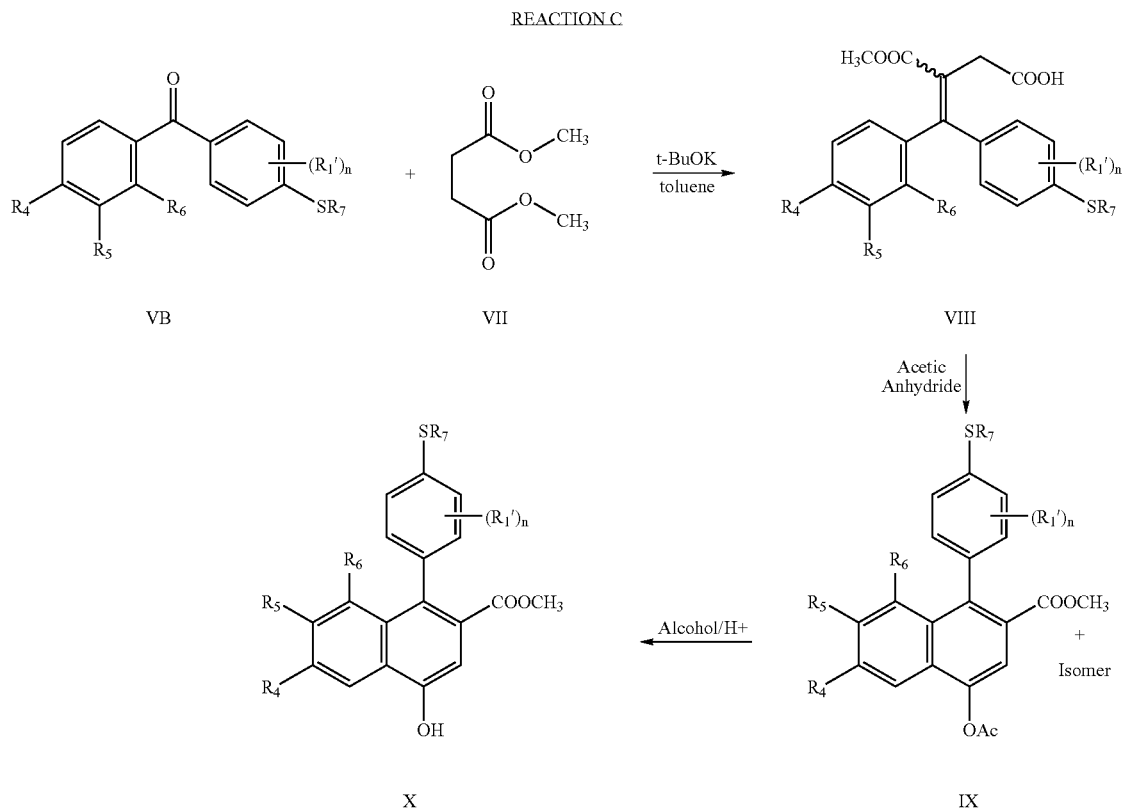

In Reaction D, a further non-limiting alternate method of preparing the compound represented by graphic formula X is disclosed. The substituted naphthol represented by graphic formula XI is reacted with dihydropyran (DHP)in methylene chloride in the presence of an acid (H+), such as para-toluene sulfonic acid (pTSA) or pyridium para toluene sulfonate (pPTS), to a form the tetrahydropyran (THP) substituted naphthol represented by graphic formula XII. The compound represented by graphic formula XII is reacted with methyl iodide in the presence of anhydrous potassium carbonate in a suitable solvent such as anhydrous acetone to form compounds represented by graphic formula XIII. Alkylating reactions are further described in "Organic Synthesis". Vol. 31 pages 90-93, John Wiley & Sons, Inc., New York, N.Y.

When an ester and methoxy group are arranged as such on the compound of graphic formula XIII, the methoxy substituent can be converted to a variety of different groups by reaction with Grignard reagents, represented by R"MgX' wherein R" is an organic group and X' is a halogen or by reaction with organolithium reagents. For example, the compound of graphic formula XIII is reacted with a benzene having $SR_7$ as the $R_1$ substituent and $(R_1,)_n$ in a suitable solvent such as anhydrous tetrahydrofuran to form compounds represented by graphic formula X. This ester-mediated nucleophilic aromatic substitution reaction is done by methods known to those skilled in the art, for example, as further described in Synthesis, January 1995, pages 41-43; The Journal of Chemical Society Perkin Transaction I, 1995, pages 235-241.

REACTION D

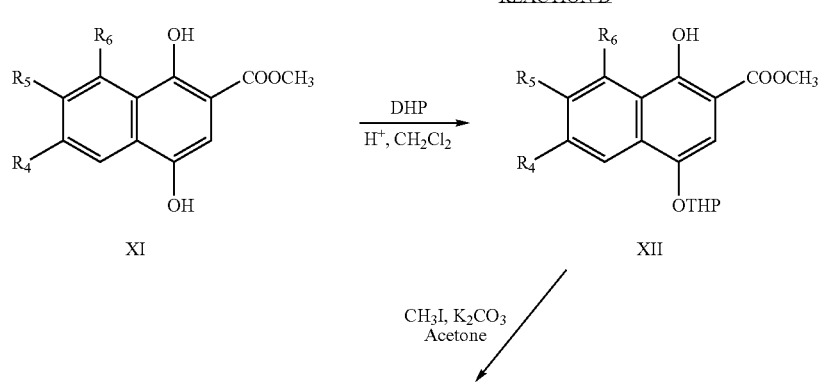

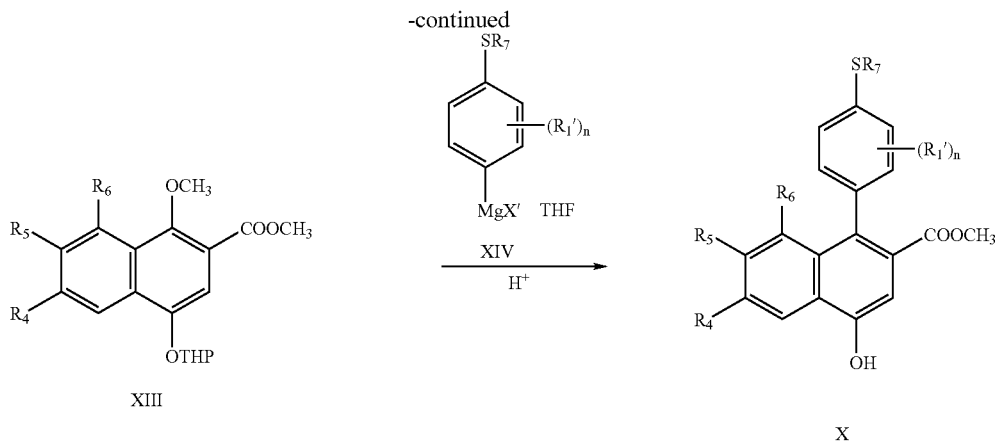

Further by way of non-limiting illustration in Reaction E, the compound represented by graphic formula XA having a fluoro substituent (or any other halo or similar replacement type substituent) in the $R_1$ position is treated with sodium hydroxide in boiling ethanol/water to form the carboxynaphthol of graphic formula XV. The compound represented by graphic formula XV is cyclized by heating, e.g., from about 110 to about 200° C., in the presence of an acid, such as dodecylbenzene sulfonic acid (DBSA), to a hydroxy-substituted benzo-fused fluorenone represented by graphic formula XVI. See the article by F. G. Baddar et al, in the J. Chem. Soc., page 986, 1958.

The compound represented by graphic formula XVI can be reacted with a lithium salt of $N(R_{15})R_{16}$ (or any amine type substituent) represented by graphic formula XVII in a solvent such as tetrahydrofuran to produce an amino substituent as $R_1$ on the compound represented by graphic formula XVIII.

REACTION E

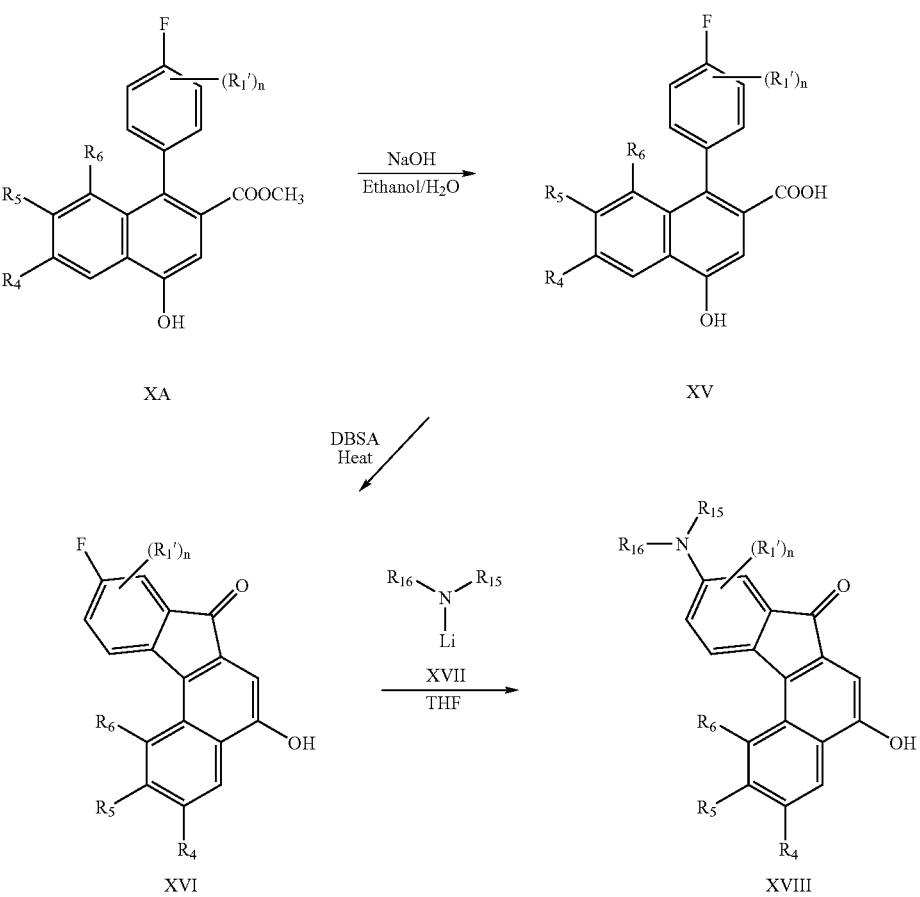

In Reaction F, non-limiting methods for the preparation of materials having $R_2$ or $R_3$ substituents as well as an amino group as $R_1$ are disclosed. The compound represented by graphic formula XB, having the $R_2$ (or $R_3$) substituent present, is reacted with a Grignard reagent such as $R_3MgX'$ (or $R_2MgX'$) or a lithium reagent having an $R_3$ (or $R_2$) substituent to produce the compound represented by graphic formula XB. Compound XB is treacted with acid in toluene until cyclized to produce the compound of graphic formula XVIA. The compound represented by graphic formula XVIA has fluorine, but in one non-limiting embodiment, could have any Leaving Group such as a different halogen, alkoxy or a sulfonate such as p-toluenesulfonate or tosyl, brosyl, mesyl or trifyl. The compound represented by graphic formula XVIA is reacted with a lithium salt of an amine represented by graphic formula XVII in a solvent such as tetrahydrofuran to produce an amino substituent as $R_1$ on the compound represented by graphic formula XVIIIA.

Further by way of non-limiting illustration in Reaction G, the compound represented by graphic formula IXX is coupled with a propargyl alcohol represented by graphic formula VI in the presence of a catalytic amount of an acid, e.g., DBSA or pTSA, in a suitable solvent such as trichloromethane. This coupling reaction results in the indeno-fused naphthopyran represented by graphic formula IA. The compound represented by graphic formula IA is reacted with a Grignard reagent such as $R_2MgX'$ (or $R_3MgX'$) or a lithium reagent having an $R_2$ (or $R_3$) substituent to produce the compound represented by graphic formula IB. Subsequent reaction of the compound represented by graphic formula IB with an alcohol having a substituent $R_8$ in the presence of an acid such as hydrochloric acid results in the compound represented by graphic formula IC.

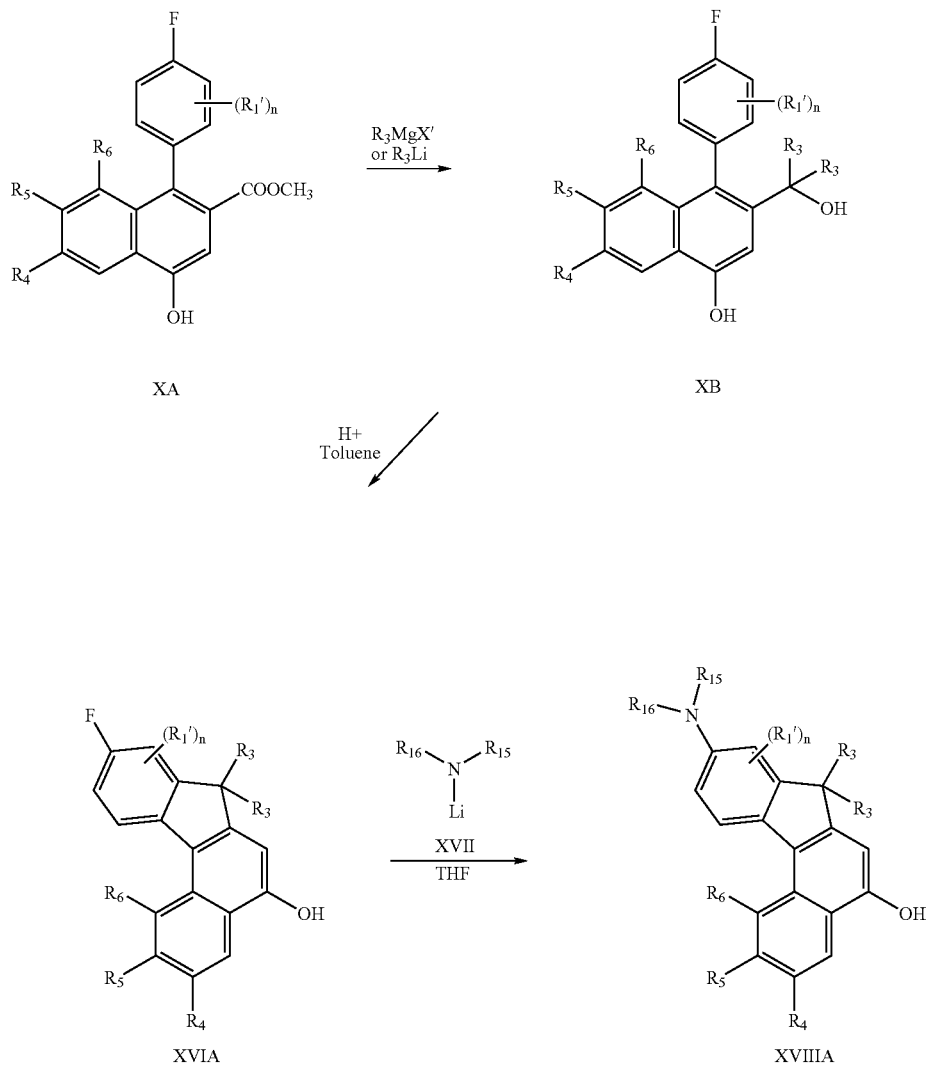

REACTION F

REACTION G

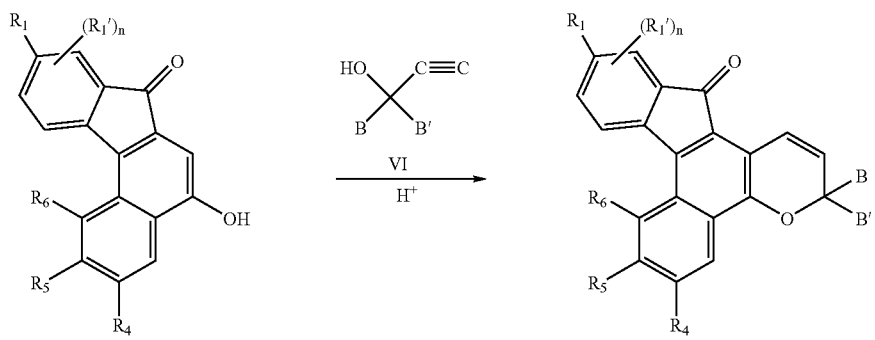

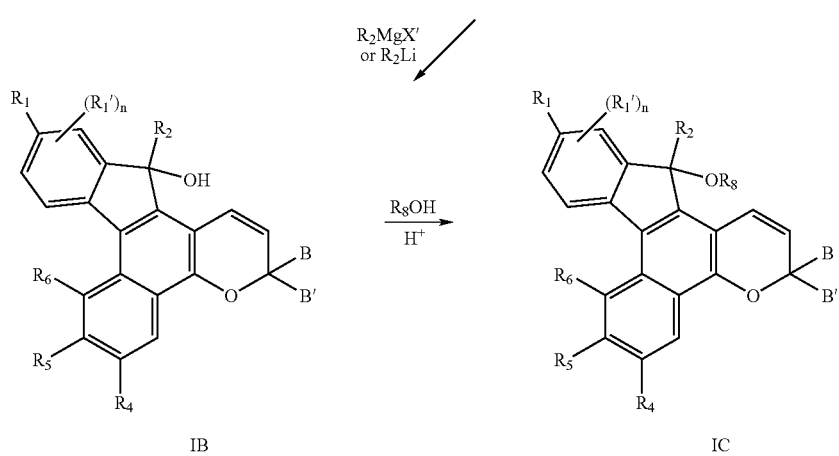

Further by way of non-limiting illustration in Reaction H, the compound represented by graphic formula IXXA is coupled with a propargyl alcohol represented by graphic formula VI in the presence of a catalytic amount of an acid, e.g., DBSA, in a suitable solvent such as trichloromethane. This coupling reaction results in the indeno-fused naphthopyran represented by graphic formula ID.

REACTION H

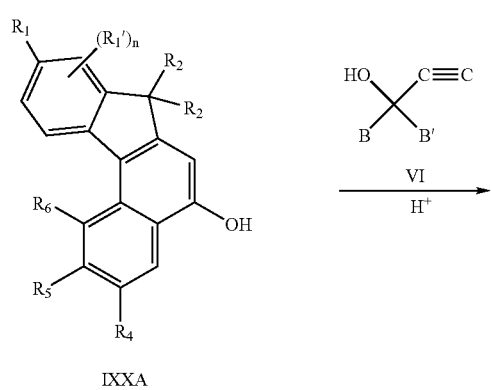

Further by way of non-limiting illustration in Reaction I, a substituted benzophenone represented by graphic formula VC having methoxy as the $R_1$ substituent and $R_1$, located at what will become the 11 position of the indeno-fused naphthopyran is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIIIA. A mixture of cis and trans half esters forms, which then undergoes cyclodehydration in the presence of acetic anhydride to form a mixture of acetoxynaphthalenes. Further purification to isolate the distinct isomer represented by graphic formula IXA may be desirable. This product is hydrolyzed in an alcoholic solution, followed by treatment with aqueous hydrochloric acid (H+) to form the carboxynaphthol represented by graphic formula XC.

REACTION I

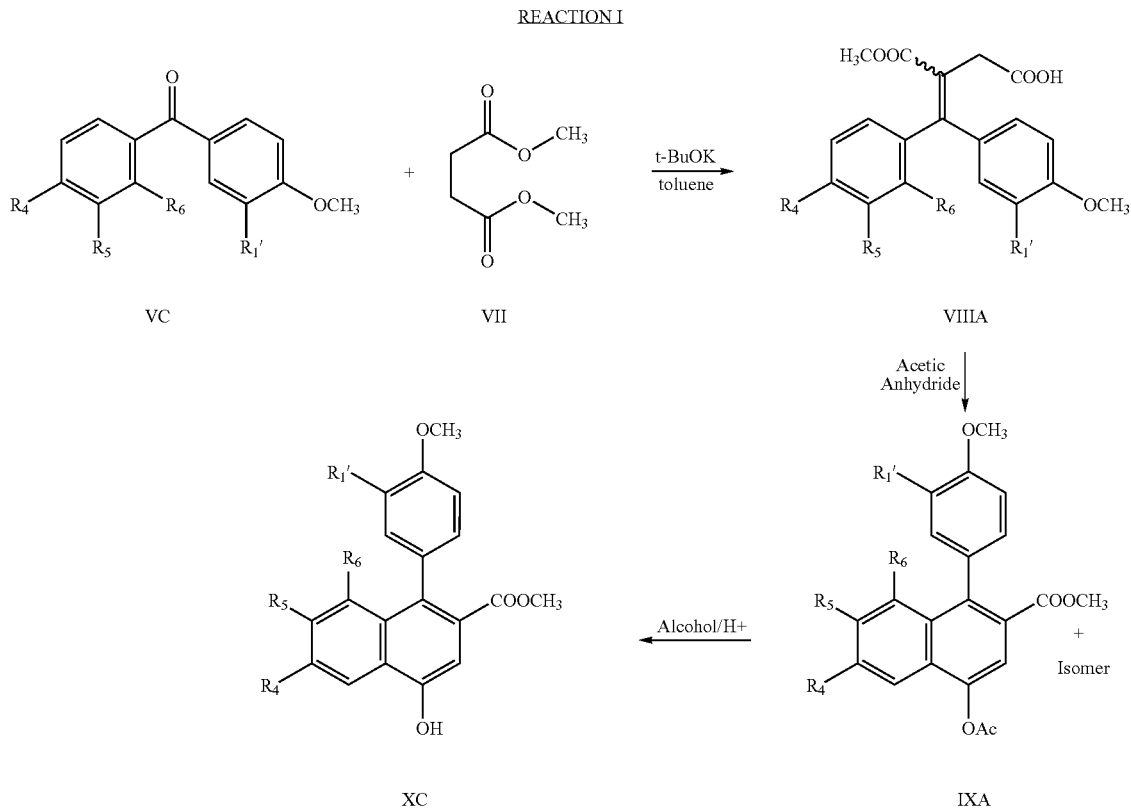

In Reaction J, non-limiting methods for the preparation of materials having $R_2$ (or $R_3$) substituents as well as an amino group as $R_1$ are disclosed. The compound represented by graphic formula XC, is reacted with a Grignard reagent such as $R_3MgX'$ (or $R_2MgX'$) or a lithium reagent having an $R_3$ (or $R_2$) substituent to produce the compound represented by graphic formula XD. Such reactions are further described in the article "Direct Substitution of Aromatic Ethers by Lithium Amides. A New Aromatic Amination Reaction" by Wolter ten Hoeve et al, J. Org. Chem. 1993, 58, 5101-5106, which article is incorporated herein by reference. Compound XD is treated with acid in toluene until cyclized to produce the compound of graphic formula XVIB. The compound represented by graphic formula XVIB is reacted with a lithium salt of an amine represented by graphic formula XVII in a solvent such as tetrahydrofuran to produce an amino substituent as $R_1$ on the compound represented by graphic formula XVIIIB.

REACTION J

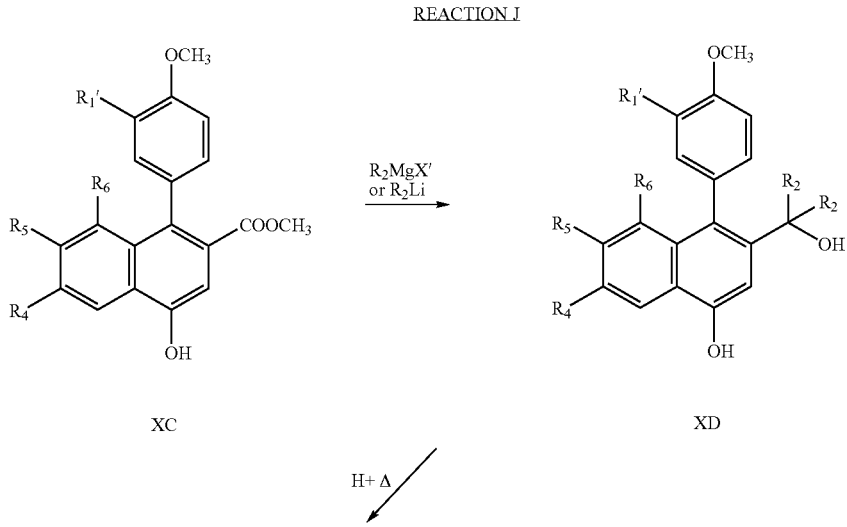

-continued

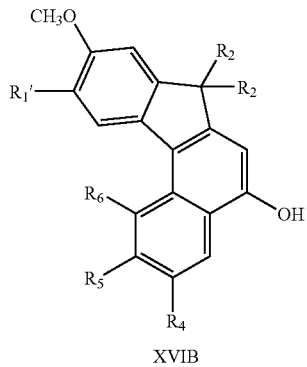

XVIB

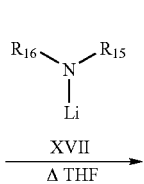

XVII
Δ THF

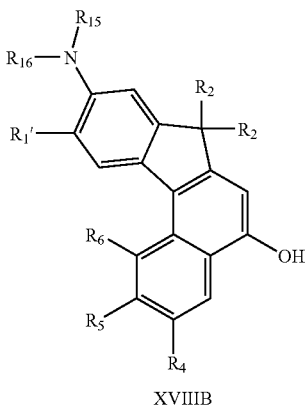

XVIIIB

Further by way of non-limiting illustration in Reaction K, the compound represented by graphic formula XVIIIB is coupled with a propargyl alcohol represented by graphic formula VI in the presence of a catalytic amount of an acid, e.g., DBSA, in a suitable solvent such as trichloromethane. This coupling reaction results in the indeno-fused naphthopyran represented by graphic formula IE.

REACTION K

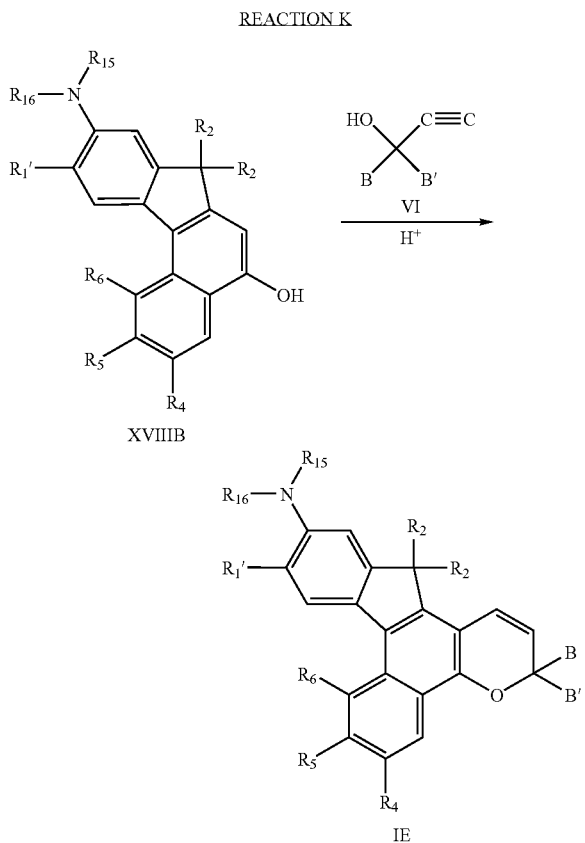

The naphthols represented by graphic formula IXXA and graphic formula XVIA (modified by having the fluoro substituent replaced with a Leaving Group that includes halo, alkoxy or sulfonate groups as discussed hereinbefore) are useful, in one non-limiting embodiment, as intermediates in the preparation of the photochromic materials of the present invention. Specific naphthols that are included within the range of materials described by the aforementioned graphic formulae, in one non-limiting embodiment, are the naphthols of graphic formulae XVIA, XVIIIA and XVIIIB.

Non-limiting examples of the naphthols within the scope of the invention are chosen from the following:

(a) 7,7-dimethyl-5-hydroxy-9-fluoro-7H-benzo[C]fluorene;

(b) 7-dimethyl-7-methoxy-5-hydroxy-9-fluoro-7H-benzo[C]fluorene;

(c) 7,7-dimethyl-5-hydroxy-9-morpholino-7H-benzo[C]fluorene;

(d) 7,7-dimethyl-5-hydroxy-10-methoxy-9-morpholino-7H-benzo[C]fluorene;

(e) 7-dimethyl-7-methoxy-5-hydroxy-9-dimethylamino-7H-benzo[C]fluorene;

(f) 7-ethyl-7-methoxy-5-hydroxy-9-piperidino-7H-benzo[C]fluorene;

(g) 7,7-dimethyl-5-hydroxy-9-piperidino-7H-benzo[C]fluorene;

(h) 7,7-dimethyl-3-methoxy-5-hydroxy-9-morpholino-7H-benzo[C]fluorene;

(i) 7,7-dimethyl-3,4-dimethoxy-5-hydroxy-9-morpholino-7H-benzo[C]fluorene;

(j) 7,7-dimethyl-3-methoxy-4-methyl-5-hydroxy-9-morpholino-7H-benzo[C]fluorene;

(k) 7,7-dimethyl-5-hydroxy-9-phenylthio-7H-benzo[C]fluorene;

(l) 7-phenyl-7-hydroxy-3-methoxy-4-methyl-5-hydroxy-9-morpholino-7H-benzo[C]fluorene;

(m) 7-ethyl-7-methoxy-5-hydroxy-9-phenylthio-7H-benzo[C]fluorene; or (n) mixtures thereof.

Non-limiting examples of naphthopyrans within the scope of the invention are chosen from the following:

(a) 3,3-di(4-methoxyphenyl)-11-morpholino-13,13-dimethyl-3H,13H-indeno[2',3 ':3,4]naphtho-[1,2-b]pyran;

(b) 3-phenyl-3-(4-morpholino-phenyl)-11-morpholino-13,13-dimethyl-3H,13H-indeno[2',3':3,4]naphtho-[1,2-b]pyran;

(c) 3,3-di(4-(2-methoxyethoxyphenyl))-11-morpholino-13,13-dimethyl-3H,13H-indeno[2',3':3,4]naphtho[1,2-b]pyran;

(d) 3,3-di(4-methoxyphenyl)-11-morpholino-13-hydroxy-13-ethyl-3H,13H-indeno[2',3':3,4]naphtho[1,2-b]pyran;

(e) 3,3-di(4-methoxyphenyl)-11-methoxy-11-morpholino-13,13-dimethyl-3H,13H-indeno[2',3':3,4]naphtho[1,2-b]pyran;

(f) 3-(4-methoxyphenyl)-3-(4-morpholinophenyl)-10-methoxy-11-morpholino-13,13-dimethyl-3H,13H-indeno[2',3':3,4] naphtho[1,2-b]pyran;

(g) 3-(3,4-dimethoxyphenyl)-3-(4-methoxyphenyl)-11-morpholino -13,13-dimethyl-3H,13H-indeno[2',3':3,4]naphtho[1,2-b]pyran; or (h) 3-(4-methoxyphenyl)-3-(4-morpholinophenyl)-11-morpholino -13,13-dimethyl-3H,13H-indeno[2',3':3,4]naphtho[1,2-b]pyran.

Each of the naphthopyran materials with or without the other photochromic materials described herein can be used in amounts (or in a ratio) that can vary widely. Generally, an amount is used so that a host material or substrate to which the photochromic materials is associated, exhibits a desired resultant color, e.g., a substantially neutral color when activated with unfiltered sunlight, e.g., as near a neutral color as possible given the colors of the activated photochromic materials. The photochromic materials, could be used to produce articles having a wide range of colors, e.g., pink. Further discussion of neutral colors and ways to describe colors can be found in U.S. Pat. No. 5,645,767 column 12, line 66 to column 13, line 19.

In one non-limiting embodiment, it is contemplated that photochromic material of the present invention can be used alone or in combination with other such materials of the present invention, or in combination with one or more other organic photochromic materials, e.g., photochromic materials having at least one activated absorption maxima within the range of between about 400 and 700 nanometers.

In another non-limiting embodiment, the other photochromic materials can include the following classes of materials: chromenes, e.g., naphthopyrans, benzopyrans, indenonaphthopyrans, phenanthropyrans or mixtures thereof; spiropyrans, e.g., spiro(benzindoline)naphthopyrans, spiro(indoline) benzopyrans, spiro(indoline)naphthopyrans, spiro(indoline) quinopyrans and spiro(indoline)pyrans; oxazines, e.g., spiro (indoline)naphthoxazines, spiro(indoline) pyridobenzoxazines, spiro(benzindoline) pyridobenzoxazines, spiro(benzindoline)naphthoxazines and spiro(indoline)benzoxazines; mercury dithizonates, fulgides, fulgimides and mixtures of such photochromic compounds.

Such photochromic materials and complementary photochromic materials are described in U.S. Pat. No. 4,931,220 at column 8, line 52 to column 22, line 40; U.S. Pat. No. 5,645,767 at column 1, line 10 to column 12, line 57; U.S Pat. No. 5,658,501 at column 1, line 64 to column 13, line 17; U.S. Pat. No. 6,153,126 at column 2, line 18 to column 8, line 60; U.S. Pat. No. 6,296,785 at column 2, line 47 to column 31, line 5; U.S. Pat. No. 6,348,604 at column 3, line 26 to column 17, line 15; and U.S. Pat. No. 6,353,102 at column 1, line 62 to column 11, line 64, the disclosures of the aforementioned patents are incorporated herein by reference. Spiro(indoline) pyrans are also described in the text, *Techniques in Chemistry*, Volume III, "Photochromism", Chapter 3, Glenn H. Brown, Editor, John Wiley and Sons, Inc., New York, 1971.

In a further non-limiting embodiment, the other photochromic materials can be polymerizable photochromic materials, such as polymerizable naphthoxazines disclosed in U.S. Pat. No. 5,166,345 at column 3, line 36 to column 14, line 3; polymerizable spirobenzopyrans disclosed in U.S. Pat. No. 5,236,958 at column 1, line 45 to column 6, line 65; polymerizable spirobenzopyrans and spirobenzothiopyrans disclosed in U.S. Pat. No. 5,252,742 at column 1, line 45 to column 6, line 65; polymerizable fulgides disclosed in U.S. Pat. No. 5,359,085 at column 5, line 25 to column 19, line 55; polymerizable naphthacenediones disclosed in U.S. Pat. No. 5,488,119 at column 1, line 29 to column 7, line 65; polymerizable spirooxazines disclosed in U.S. Pat. No. 5,821,287 at column 3, line 5 to column 11, line 39; polymerizable polyalkoxylated naphthopyrans disclosed in U.S. Pat. No. 6,113,814 at column 2, line 23 to column 23, line 29; and the polymerizable photochromic compounds disclosed in WO97/05213 and allowed U.S. application Ser. No. 09/828,260 filed Apr. 6, 2001. The disclosures of the aforementioned patents on polymerizable photochromic materials are incorporated herein by reference.

Other non-limiting embodiments of photochromic materials that can be used include organo-metal dithiozonates, e.g., (arylazo)-thioformic arylhydrazidates, e.g., mercury dithizonates which are described in, for example, U.S. Pat. No. 3,361,706 at column 2, line 27 to column 8, line 43; and fulgides and fulgimides, e.g., the 3-furyl and 3-thienyl fulgides and fulgimides, which are described in U.S. Pat. No. 4,931,220 at column 1, line 39 through column 22, line 41, the disclosures of which are incorporated herein by reference.

An additional non-limiting embodiment of the other photochromic materials is a form of organic photochromic material resistant to the effects of a polymerization initiator that can also be used in the photochromic articles of the present invention. Such organic photochromic materials include photochromic compounds in admixture with a resinous material that has been formed into particles and encapsulated in metal oxides, which are described in U.S. Pat. Nos. 4,166,043 and 4,367,170 at column 1 line 36 to column 7, line 12, which disclosure is incorporated herein by reference.

The photochromic materials described herein, e.g., the photochromic naphthopyrans of the present invention and other photochromic materials, can be chosen from a variety of materials. Non-limiting examples include: of course, a single photochromic compound; a mixture of photochromic compounds; a material comprising at least one photochromic compound, such as a plastic polymeric resin or an organic monomeric or oligomeric solution; a material such as a monomer or polymer to which at least one photochromic compound is chemically bonded; a material comprising and/or having chemically bonded to it at least one photochromic compound, the outer surface of the material being encapsulated (encapsulation is a form of coating), for example with a polymeric resin or a protective coating such as a metal oxide that prevents contact of the photochromic material with external materials such as oxygen, moisture and/or chemicals that have a negative effect on the photochromic material, such materials can be formed into a particulate prior to applying the protective coating as described in U.S. Pat. Nos. 4,166,043 and 4,367,170; a photochromic polymer, e.g., a photochromic polymer comprising photochromic compounds bonded together; or mixtures thereof.

In one non-limiting embodiment, the amount of the photochromic materials to be incorporated into a polymeric coating composition and/or polymeric host material can vary widely. Generally a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate the photochromic materials. Typically, in one non-limiting embodiment, the more photochromic incorporated, the greater is the color intensity up to a certain limit. There is a point after which the addition of any more material will not have a noticeable effect, although more material may be added, if desired.

The relative amounts of the aforesaid naphthopyran materials or combinations of naphthopyran materials and other photochromic materials used will vary and depend in part upon the relative intensities of the color of the activated species of such materials, the ultimate color desired, and the method of application to the host material and/or substrate. In one non-limiting embodiment, the amount of total photochromic material which includes naphthopyran materials, other photochromic materials or both, incorporated by imbibition into a photochromic optical host material can vary widely. For example, it can range from about 0.01 to about 2.0, e.g., from 0.05 to about 1.0, milligrams per square centimeter of surface to which the photochromic material is incorporated or applied. The amount of total photochromic material incorporated or applied to the host material can range between any combination of these values, inclusive of the recited range, e.g., 0.015 to 1.999 milligrams per square centimeter.

In another non-limiting embodiment, the total amount of photochromic material incorporated into a polymerizable composition for forming a coating or polymerizate can vary widely. For example, it can range from 0.01 to 40 weight percent based on the weight of the solids in the polymerizable composition. In alternate non-limiting embodiments, the concentration of photochromic materials can range from 0.1 to 30 weight percent, from 1 to 20 weight percent, from 5 to 15 weight percent, or from 7 to 14 weight percent. The amount of photochromic material in the coating can range between any combination of these values, inclusive of the recited range, e.g., 0.011 to 39.99 weight percent.

In one non-limiting embodiment, compatible (chemically and color-wise) fixed tint dyes, can be added or applied to the host material, e.g., polymeric substrate, polymeric coating and/or polymeric film, used to produce the photochromic article to achieve a more aesthetic result, for medical reasons, or for reasons of fashion. The particular dye selected will vary and depend on the aforesaid need and result to be achieved. In one non-limiting embodiment, the dye can be selected to complement the color resulting from the activated photochromic materials, e.g., to achieve a more neutral color or absorb a particular wavelength of incident light. In another non-limiting embodiment, the dye can be selected to provide a desired hue to the host material when the photochromic materials are in an unactivated state.

In various non-limiting embodiments, adjuvant materials can also be incorporated into the host material used to produce the photochromic article. Such adjuvants can be used, prior to, simultaneously with or subsequent to application or incorporation of the photochromic material. For example, ultraviolet light absorbers can be admixed with photochromic materials before their addition to the composition or such absorbers can be superposed, e.g., superimposed, as a coating between the photochromic article and the incident light.

Further, stabilizers can be admixed with the photochromic materials prior to their addition to the composition to improve the light fatigue resistance of the photochromic materials provided that such stabilizers do not prevent the photochromic materials from activating. Non-limiting examples of stabilizers include hindered amine light stabilizers (HALS), asymmetric diaryloxalamide (oxanilide) compounds and singlet oxygen quenchers, e.g., a nickel ion complex with an organic ligand, polyphenolic antioxidants or mixtures of such stabilizers are contemplated. In one non-limiting embodiment, they can be used alone or in combination. Such stabilizers are described in U.S. Pat. Nos. 4,720,356, 5,391,327 and 5,770,115.

The naphthopyran materials of the present invention, other photochromic materials or combinations thereof can be associated with the host material by various methods described in the art. In various non-limiting embodiments, the total amount of photochromic material can be incorporated into the host material used to form the photochromic article by various methods such as by adding the photochromic materials to one or more of the materials used to form the host material. In one non-limiting embodiment when the host material is a polymeric coating or film, the photochromic materials can be dissolved and/or dispersed in an aqueous or organic solvent prior to being incorporated into one or more of the components of the composition used to form the coating or film. Alternatively, the photochromic materials can be incorporated into the at least partially cured coating by imbibition, permeation or other transfer methods as known by those skilled in the art.

When at least partially cured polymers or polymerizates are used as the host material for the photochromic materials, various non-limiting embodiments include preparation of a photochromic article by injecting a polymerizable composition with photochromic materials with or without polymerizable substituents into a mold and polymerizing it by what, for example, is commonly referred to in the art as a cast-in-place process. In another non-limiting embodiment, photochromic materials can be added with the materials used to produce a polymeric film by extrusion or other methods known to those skilled in the art. Polymerizates, e.g., lenses, prepared by cast polymerization in the absence of a photochromic amount of a photochromic material can be used to prepare photochromic articles by applying or incorporating photochromic materials into the polymerizate by art-recognized methods.

Such non-limiting art-recognized methods include: (a) dissolving, dispersing and/or reacting the photochromic materials with or without polymerizable substituents with the materials used to form the polymerizate, e.g., addition of photochromic materials to a polymerizable composition or imbibition of the photochromic materials into the polymerizate by immersion of the polymerizate in a hot solution of the photochromic materials or by thermal transfer; (b) providing the photochromic material as a separate layer between adjacent layers of the polymerizate, e.g., as a part of a polymer film; and (c) applying the photochromic material as part of a coating or film placed or laminated on the surface of the polymerizate. The term "imbibition" or "imbibe" is intended to mean and include permeation of the photochromic materials individually or with other non-photochromic materials into the polymerizate, solvent assisted transfer absorption of the photochromic materials into a polymerizate, vapor phase transfer, and other such transfer mechanisms.

In the context of the present invention, the nature of the polymeric substrate, polymeric film or polymeric coating, collectively referred to as the polymeric composition, can vary widely. Generally the polymeric composition is such that it allows the naphthopyran materials of the present invention and other photochromic materials to reversibly transform between their "open" and "closed" forms. In one non-limiting embodiment, the polymeric composition used to produce the photochromic articles of the present invention comprises compositions adapted to provide thermoplastic or thermosetting organic polymeric materials that are described in the *Kirk-Othmer Encyclopedia of Chemical Technology*, Fourth Edition, Volume 6, pages 669 to 760, which disclosure is incorporated herein by reference. Such polymeric host materials can be transparent, translucent or opaque; but desirably are transparent or optically clear. In another non-limiting contemplated embodiment is a polymeric material that upon curing forms an at least partially cured polymeric coating chosen from polyurethanes, aminoplast resins, poly(meth) acrylates, e.g., polyacrylates and polymethacrylates, polyanhydrides, polyacrylamides, epoxy resins and polysilanes.

The various coating compositions described below are well known and are made with components and according to methods well understood and appreciated to those skilled in the art. Suitable substrates for the application of coatings containing the naphthopyran materials or a mixture of the naphthopyran materials and other photochromic materials include any type of substrate. Non-limiting examples include, paper, glass, ceramics, wood, masonry, textiles, metals and polymeric organic host materials.

The photochromic polyurethane coatings that can be used to prepare the photochromic coated articles of the present invention, in one non-limiting embodiment, can be produced by the catalyzed or uncatalyzed reaction of an organic polyol component and an isocyanate component in the presence of photochromic compound(s). Materials and methods for the preparation of polyurethanes are described in *Ullmann's Encyclopedia of Industrial Chemistry*, Fifth Edition, 1992, Vol. A21, pages 665 to 716. Non-limiting examples of methods and materials, e.g., organic polyols, isocyanates and other components, which can be used to prepare the polyurethane coating are disclosed in U.S. Pat. Nos. 4,889,413 and 6,187,444B1.

The photochromic aminoplast resin coating composition that can be used to produce the photochromic coated articles of the present invention, in one non-limiting embodiment, can be prepared by combining a photochromic material with the reaction product of a functional component(s) having at least two functional groups chosen from hydroxyl, carbamate, urea or a mixture thereof and an aminoplast resin, e.g., crosslinking agent as described in U.S. Pat. Nos. 4,756,973, 6,432,544B1 and 6,506,488.

Photochromic polysilane coating compositions contemplated for use in preparing the photochromic coated articles of the present invention, in one non-limiting embodiment, are prepared by hydrolyzing at least one silane monomer such as glycidoxypropyltrimethoxysilane, vinyltrimethoxysilane, methacryloxypropyltrimethoxysilane, tetramethoxysilane, tetraethoxysilane and/or methyltrimethoxysilane and combining the hydrolyzate with at least one photochromic material as described in U.S. Pat. No. 4,556,605.

Photochromic poly(meth)acrylate coating compositions contemplated for use in preparing the photochromic coated articles of the present invention can be prepared, in one non-limiting embodiment, by combining photochromic compound(s) with mono-, di- or multi-functional (meth)acrylates as described in U.S. Pat. Nos. 6,025,026 and 6,150,430 and WO publication 01/02449 A2.

The polyanhydride photochromic coating composition that can be used to prepare the photochromic coated articles of the present invention can be prepared in one non-limiting embodiment, by the reaction of a hydroxyl-functional component and a polymeric anhydride-functional component in a composition including at least one organic photochromic material as described in U.S. Pat. No. 6,432,544B1. Non-limiting examples of hydroxyl-functional components, anhydride-functional component(s) and other components that can be used to prepare the polyanhydride photochromic coatings are disclosed in U.S. Pat. Nos. 4,798,745, 4,798,746 and 5,239,012.

Photochromic polyacrylamide coating compositions contemplated for use in preparing the photochromic coated articles of the present invention, in one non-limiting embodiment. can be prepared by combining a photochromic component with the free radical initiated reaction product of a polymerizable ethylenically unsaturated composition comprising N-alkoxymethyl(meth)acrylamide and at least one other copolymerizable ethylenically unsaturated monomer as described in U.S. Pat. No. 6,060,001. Methods for preparing N-alkoxymethyl(meth)acrylamide functional polymer are described in U.S. Pat. No. 5,618,586.

The photochromic epoxy resin coating compositions that can be used to prepare the photochromic coated articles of the present invention, in one non-limiting embodiment, can be prepared by combining photochromic compound(s), epoxy resins or polyepoxides and curing agents as described in U.S. Pat. Nos. 4,756,973 and 6,268,055B1.

In another non-limiting embodiment, the types of photochromic polymeric coatings comprising the film-forming polymers and the naphthopyran materials of the present invention with or without other photochromic compounds include paints, e.g., a pigmented liquid or paste used for the decoration, protection and/or the identification of a substrate; and inks, e.g., a pigmented liquid or paste used for writing and printing on substrates such as in producing verification marks on security documents, e.g., documents such as banknotes, passport and drivers' licenses, for which authentication or verification of authenticity may be desired.

Application of the polymeric coating can be by any of the methods used in coating technology, non-limiting examples include, spray coating, spin coating, spin and spray coating, spread coating, curtain coating, dip coating, casting or roll-coating and methods used in preparing overlays, such as the method of the type described in U.S. Pat. No. 4,873,029. The application method selected also depends on the thickness of the desired coating.

The thickness of the coatings on the photochromic articles of the present invention can vary widely. Coating having a thickness ranging from 1 to 50 microns can be applied by the methods used in coating technology. Coating of a thickness greater than 50 microns can require the application of multiple coatings or molding methods typically used for overlays. In alternate non-limiting embodiments, the coating may range in thickness from 1 to 10,000 microns, from 5 to 1000, from 8 to 400, or from 10 to 250 microns. The thickness of the polymeric coating can range between any combination of these values, inclusive of the recited range, e.g., a thickness of from 20 to 200 microns.

Following application of the polymeric coating to the surface of the substrate, in one non-limiting embodiment, the coating is at least partially cured. In another non-limiting embodiment, the methods used for curing the photochromic polymeric coating include the methods used for forming an at least partially cured polymer. Such methods include radical polymerization, thermal polymerization, photopolymerization or a combination thereof. Additional non-limiting methods include irradiating the coated substrate or at least partially cured polymer with infrared, ultraviolet, gamma or electron radiation so as to initiate the polymerization reaction of the polymerizable components with or without a catalyst or initiator. This can be followed by a heating step.

In one non-limiting embodiment, if required and if appropriate, the surface of the substrate to be coated is cleaned prior to applying the photochromic polymeric coating to produce the photochromic article of the present invention. This can be done for the purposes of cleaning and/or promoting adhesion of the coating. Effective treatment techniques for plastics and glass are known to those skilled in the art.

In some non-limiting embodiments, it may be necessary to apply a primer to the surface of the substrate before application of the photochromic polymeric coating. The primer can serve as a barrier coating to prevent interaction of the coating ingredients with the substrate and vice versa, and/or as an adhesive layer to adhere the photochromic polymeric coating to the substrate. Application of the primer can be by any of the methods used in coating technology such as, for example, spray coating, spin coating, spin and spray coating, spread coating, dip coating, casting or roll-coating.

The use of protective coatings, some of which can contain polymer-forming organosilanes, as primers to improve adhesion of subsequently applied coatings has been described in U.S. Pat. No. 6,150,430, which disclosure is incorporated herein by reference. In one non-limiting embodiment, non-tintable coatings are used. Non-limiting examples of commercial coating products include SILVUE® 124 and HI-GARD® coatings, available from SDC Coatings, Inc. and PPG Industries, Inc., respectively. In addition, depending on the intended use of the coated article, in one non-limiting embodiment, it can be necessary to apply an appropriate protective coating(s), such as an abrasion resistant coating and/or coatings that can serve as oxygen barriers, onto the exposed surface of the coating composition to prevent scratches from the effects of friction and abrasion and interactions of oxygen with the photochromic materials, respectively.

In some cases, the primer and protective coatings are interchangeable, e.g., the same coating can be used as the primer and the protective coating(s). Non-limiting examples of hardcoats include those based on inorganic materials such as silica, titania and/or zirconia as well as organic hardcoats of the type that are ultraviolet light curable. In one non-limiting embodiment, such protective coatings can be applied to the surface of photochromic articles comprising at least partially cured polymers containing photochromic materials.

In another non-limiting embodiment, the article of the present invention comprises a substrate to which a primer is applied followed by the photochromic polymeric coating and a protective hardcoat. In a further non-limiting embodiment, the protective hardcoat is a polysilane, e.g., an organosilane hardcoat.

In additional non-limiting embodiments, other coatings or surface treatments, e.g., a tintable coating, at least a partially antireflective coating, etc., can also be, applied to the photochromic articles of the present invention. An antireflective coating, e.g., a monolayer or multilayer of metal oxides, metal fluorides, or other such materials, can be deposited onto the photochromic articles, e.g., lenses, of the present invention through vacuum evaporation, sputtering, or some other method.

In a further non-limiting embodiment, the photochromic article comprising an at least partially cured polymer and a photochromic a photochromic amount of at least one indeno [2',3':3,4]naphtho[1,2-b]pyran with or without other photochromic material further comprises a superstrate, e.g., a film or sheet comprising at least one organic polymeric material. The photochromic material can be located in the superstrate, the at least partially cured polymer or both. The organic polymeric material of the superstrate is the same as the organic polymeric material described hereinafter as the substrate or host material. Non-limiting examples of the organic polymeric materials include thermosetting or thermoplastic materials, for example a thermoplastic polyurethane superstrate.

In a still further non-limiting embodiment, the superstrate can be connected to the polymer surface directly, but does not become thermally fused to the substrate. In another non-limiting embodiment, the superstrate can be adherringly bonded to the substrate by becoming thermally fused with the subsurface of the substrate. General conditions under which superstrates are adherringly bonded to a substrate are known to those skilled in the art. Non-limiting conditions for adherringly laminating a superstrate to a substrate include heating to a temperature of from 250-350° F. (121-177° C.) and applying pressure of from 150 to 400 pounds per square inch (psi) (1034 to 2758 kPa). Sub-atmospheric pressures, e.g., a vacuum, can also be applied to draw down and conform the superstrate to the shape of the substrate as known to those skilled in the art. Non-limiting examples include applying at a sub-atmospheric pressure within the range of from 0.001 mm Hg to 20 mm Hg (0.13 Pa to 2.7 kPa).

After a laminate comprising a superstrate applied to as least one surface of a substrate is formed, it can further comprise a protective coating or film superposed onto the superstrate. Such a protective coating or film, in one non-limiting embodiment, serves as an at least partially abrasion resistant coating or film. Non-limiting types of protective coatings include the aforedescribed hardcoats that are curable by ultraviolet radiation and/or that contain organosilanes. The thickness of the protective coating can vary widely and include the aforementioned range for the photochromic polymeric coatings. Non-limiting types of protective films include those made of organic polymeric materials such as thermosetting and thermoplastic materials. In another non-limiting embodiment, the protective film is a thermoplastic film made of polycarbonate. The thickness of the protective film or sheet can vary widely. Typically, such films have a thickness of from 1 to 20 mils (0.025 to 0.5 mm).

The host material for the naphthopyran materials of the present invention with or without other photochromic materials will usually be transparent, but may be translucent or even opaque. The host material need only be pervious to that portion of the electromagnetic spectrum, which activates the photochromic material, e.g., that wavelength of ultraviolet (UV) light that produces the open or colored form of the photochromic and that portion of the visible spectrum that includes the absorption maximum wavelength of the photochromic in its UV activated form, e.g., the open form. In one contemplated non-limiting embodiment, the host color should not be such that it masks the color of the activated form of the photochromic materials, e.g., so the change in color is readily apparent to the observer. Compatible tints may be applied to the host material as described in U.S. Pat. No. 5,645,767 in column 13, line 59 to column 14, line 3.

In one contemplated non-limiting embodiment, the polymeric organic host material can be a solid transparent or optically clear material, e.g., materials having a luminous transmittance of at least 70 percent and are suitable for optical applications, such as optical elements chosen from plano and ophthalmic lenses, ocular devices such as ophthalmic devices that physically reside in or on the eye, e.g., contact lenses and intraocular lenses, windows, automotive transparencies, e.g., windshields, aircraft transparencies, plastic sheeting, polymeric films, etc.

Non-limiting examples of polymeric organic materials which can be used as a host material for the naphthopyran materials of the present invention with or without other photochromic materials or as a substrate for the photochromic polymeric coating include: poly(meth)acrylates, polyurethanes, polythiourethanes, poly(urea-urethanes), thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral, poly(vinyl acetate), cellulose acetate, cellulose propionate, cellulose butyrate, cellulose acetate butyrate, polystyrene or polymers, such as homopolymers and copolymers prepared by polymerizing monomers chosen from bis(allyl carbonate) monomers, styrene monomers, diisopropenyl benzene monomers, vinylbenzene monomers, e.g., those described in U.S. Pat. No. 5,475,074, diallylidene pentaerythritol monomers, polyol (allyl carbonate) monomers, e.g., diethylene glycol bis(allyl carbonate), vinyl acetate monomers, acrylonitrile monomers, mono- or polyfunctional, e.g., di- or multi-functional, (meth) acrylate monomers such as ($C_1$-$C_{12}$)alkyl (meth)acrylates, e.g., methyl (meth)acrylate, ethyl (meth)acrylate, butyl (meth)acrylate etc., poly(oxyalkylene)(meth)acrylate, poly (alkoxylated phenol (meth)acrylates), diethylene glycol (meth)acrylates, ethoxylated bisphenol A (meth)acrylates, ethylene glycol (meth)acrylates, poly(ethylene glycol) (meth)acrylates, ethoxylated phenol (meth)acrylates, alkoxylated polyhydric alcohol (meth)acrylates, e.g., ethoxylated trimethylol propane triacrylate monomers, urethane (meth) acrylate monomers, such as those described in U.S. Pat. No. 5,373,033, or a mixture thereof. Further examples of polymeric organic host materials are disclosed in the U.S. Pat. No. 5,753,146, column 8, line 62 to column 10, line 34.

In another non-limiting embodiment, transparent copolymers and blends of transparent polymers are also suitable as polymeric materials. The host material can be an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483.

A further non-limiting embodiment is use of the naphthopyran materials of the present invention and other photochromic materials with optical organic resin monomers used to produce optically clear coatings and polymerizates, e.g., materials suitable for optical applications, such as for example plano and ophthalmic lenses, windows, and automotive transparencies. Examples of non-limiting embodiments include polymerizates of optical resins sold by PPG Industries, Inc. as TRIVEX monomers and under the CR-designation, e.g., CR-307, CR-407 and CR-607 and the resins used to prepare hard or soft contact lenses. Methods for producing both types of contact lenses are disclosed in U.S. Pat. No. 5,166,345, column 11, line 52, to column 12, line 52.

Further non-limiting embodiments of optical resins include the resins used to form soft contact lenses with high moisture content described in U.S. Pat. No. 5,965,630 and extended wear contact lenses described in U.S. Pat. No. 5,965,631.

The present invention is more particularly described in the following examples which are intended as illustration only, since numerous modifications and variations therein will be apparent to those skilled in the art.

Examples 1-8 are of the photochromic materials of the present invention. Comparative Examples (CE) 1-5 represent photochromic materials prepared by methods disclosed in U.S. Pat. Nos. 5,645,767 and 6,296,785B1. Example 9 describes the Indenonaphthopyran Photochromic Performance Test.

EXAMPLE 1

Step 1

Methylene chloride (2 liters (L)), 1,4-dihydroxy-2-phenoxycarbonyl-naphthalene (384 grams) and 152 grams of dihydropyran were added to a 3 L multi-necked flask at room temperature. The mixture was placed on a magnetic stirrer, and a solution of dodecylbenzenesulfonic acid (1.4 grams, in 15 milliliters (mL) of methylene chloride) was added with stirring. After 1 hour of mixing, the completed reaction was quenched by adding triethylamine (2.7 grams) and potassium carbonate (2.7 grams). The suspension was vacuum filtered and the solvent was removed by rotary evaporation. The recovered product was a thick oil. All of it was used as is, without purification, in the next step.

Step 2

The oily product from step 1 was added to a flask and dissolved in acetone (750 mL). Potassium carbonate (200 grams) and iodomethane (220 mL) were added and the reaction was stirred and heated to 40° C. The reaction was gradually heated to reflux and iodomethane was added 4 times, each time with 1 equivalent, until the reaction was complete. The mixture was vacuum filtered and the solvent was removed by rotary evaporation to yield a concentrated liquid. The liquid was poured into 2 L of water and formed a brown precipitate. The brown precipitate was vacuum filtered, dissolved in 2.5 L of ethyl acetate and the solvent was removed by rotary evaporation to yield 200 mL of solution. The solution was poured into 3:1 hexane:ethyl acetate to induce crystallization. Brown crystals (420 grams) of product were collected. A nuclear magnetic resonance (NMR) spectrum showed the product to have a structure consistent with 4-tetrahydropyranyloxy-1-methoxy-2-phenoxycarbonyl naphthalene.

Step 3

The product of Step 2, 4-tetrahydropyranyloxy-1-methoxy-2-phenoxycarbonyl naphthalene (200 grams) and tetrahydrofuran (800 mL) were added to a 3 L multi-necked flask and stirred at 0° C. under a nitrogen blanket. To the reaction mixture was added a 1 molar (M) fluorophenylmagnesium bromide solution (690 mL) drop-wise over a 1 hour period. After an additional 4.5 hours of stirring, the reaction mixture was poured into 1.5 L of water and acidified to pH 2. After individual phase layers formed, the layers were separated and the aqueous layer was extracted 2 times, each with 200 mL of ethyl acetate. The organic layers were combined, washed with water and the solvent was removed by rotary evaporation to yield a wet red solid. The red solid was added to a flask containing methanol (500 mL) and 12.1 M hydrochloric acid (5 mL), and the resulting solution was heated to reflux for 1 hour. After cooling and setting overnight, the crystals that formed were collected by vacuum filtration and washed with hexane to yield 102 grams of reddish-orange crystals. An NMR spectrum showed the product to have a structure consistent with 4-hydroxy-1-(4-fluorophenyl)-2-phenoxycarbonyl naphthalene.

Step 4

The product of Step 3, 4-hydroxy-1-(4-fluorophenyl)-2-phenoxycarbonyl naphthalene (148 grams) and anhydrous THF (500 mL) were added to a 3 L multi-necked flask and placed on magnetic stirrer under nitrogen and stirred. The solution was cooled to 0° C. and a 1.6 M methyl lithium solution (1.05 L) was added over 1 hour with stirring. After an additional 1.5 hours of stirring, the completed reaction was poured into 2 L of ice water and allowed to set overnight. The resulting mixture was acidified to pH 4 and the phases that formed into layers were separated. The aqueous layer was extracted 3 times, each with 200 mL of ethyl acetate. The organic layers were combined, washed with water and the solvent was removed by rotary evaporation to yield a 132 g of dark oil. The material was used directly in the next step.

Step 5

The product from Step 4 (132 grams), xylenes (1.5 L) and dodecylbenzenesulfonic acid (9.2 grams) were added to a flask and heated to reflux. After 5 hours, the reaction mixture was cooled to room temperature and washed with a 5 weight percent solution of sodium bicarbonate (300 mL). The resulting emulsion was allowed to set overnight and the phase layers that formed were separated. The organic layer was dried over magnesium sulfate and the solvent was removed by rotary evaporation to yield a concentrated liquid. The concentrated liquid was eluted through a small silica plug column with 30:1 hexane: ethyl acetate. The solvent was removed from the resulting eluant by rotary evaporation to yield an oil. Crystallization was induced with toluene and hexane to yield 28 grams of a light tam product. An NMR spectrum showed the product to have a structure consistent with 7,7-dimethyl-5-hydroxy-9-fluoro-7H-benzo[C]fluorene.

Step 6

Anhydrous tetrahydrofuran (600 mL) and morpholine (70 mL) were added to a 3 L multi-necked flask which was placed on a magnetic stir under nitrogen and cooled to 0° C. A 1.6 M methyllithium solution (450 mL) was added drop-wise over a 1 hour period with stirring. After an additional 2 hours of stirring, ice was removed and the suspension was warmed to room temperature. A solution of 7,7-dimethyl-5-hydroxy-9-fluoro-7H-benzo[C]fluorine (20 grams) from Step 5 in 250 mL of anhydrous tetrahydrofuran was slowly added into the flask and stirred at 65° C. After 13 hours, reaction was cooled to room temperature and poured into 2 L of deionized water. Ethyl acetate (500 mL) was added to induce phase separation. The layers that formed were separated. The aqueous layer was made basic to pH 8 with 5 weight percent aqueous sodium hydroxide solution and extracted 2 times, each with 200 mL of ethyl acetate. The organic layers were combined, washed with water, the solvent was removed by rotary evaporation to yield an oil which was induced to crystalize in ethyl acetate. A brown precipitate (13 grams) was collected by vacuum filtration. An NMR spectrum showed the product to have a structure consistent with 7,7-dimethyl-5-hydroxy-9-morpholino-7H-benzo[c]fluorene.

Step 7

7,7-Dimethyl-5-hydroxy-9-morpholino-7H-benzo[C] fluorene (2 grams) from Step 6, 1,1-di(4-methoxyphenyl)-2-propyn-1-ol (2 grams), two drops of dodecylbenzene sulfonic acid and chloroform (50 mL) were combined in a reaction vessel and stirred at ambient temperature overnight. Water (100 mL) was added to the reaction mixture and stirred for 30 minutes. The organic layer was separated and washed with a 10 weight percent sodium hydroxide solution followed by a wash with water. The organic layer was dried over magnesium sulfate and the solvent was removed by rotary evaporation to yield a residue. The residue was chromatographed on a silica gel using chloroform as the elutant. Photochromic fractions were collected, concentrated by rotary evaporation and the resulting solid was recrystallized from diethyl ether yielding 1.3 grams of crystals having a melting point of 258-261° C. An NMR spectrum showed the product to have a structure consistent with 3,3-di(4-methoxyphenyl)-11-morpholino-13,13-dimethyl-3H,13H-indeno[2',3':3,4]naphtho [1,2-b]pyran.

EXAMPLE 2

The process of Example 1 was followed except that in Step 7, 1-phenyl-1-(4-morpholinophenyl)-2-propyn-1-ol was used instead of 1,1-di(4-methoxyphenyl)-2-propyn-1-ol. The recovered product had a melting point of 163-164° C. NMR analysis showed the product to have a structure consistent with 3-phenyl-3-(4-morpholino-phenyl)-1-morpholino-13, 13-dimethyl-3H,13H-indeno[2',3':3,4]naphtho-[1,2-b]pyran.

EXAMPLE 3

The process of Example 1 was followed except that in Step 7, 1,1-di(4-(2-methoxyethoxyphenyl))-2-propyn-1-ol was used instead of 1,1-di(4-methoxyphenyl)-2-propyn-1-ol. The recovered product had a melting point of 153-155° C. NMR analysis showed the product to have a structure consistent with 3,3 di(4-(2-methoxyethoxyphenyl))-11-morpholino-13, 13-dimethyl-3H,13H-indeno[2',3':3,4]naphtho[1,2-b]pyran.

EXAMPLE 4

Step 1

The product of Step 3 of Example 1,4-hydroxy-1-(4-fluorophenyl)-2-phenoxycarbonyl naphthalene (10 grm), a 10 weight percent aqueous sodium hydroxide solution (50 mL) and methanol (50 mL) were added to a reaction flask and heated to reflux for 3 hours and then cooled to room temperature. The reaction mixture was poured onto an aqueous solution of 4N hydrochloric acid/ice mixture (approximately 400 mL). A white precipitate formed and was collected by vacuum filtration, washed with water and was air-dried. Recrystallization from ethanol (95 weight percent) gave 1-(4-fluorophenyl)-4-hydroxy-2-naphthoic acid (7 grams).

Step 2

1-(4-Fluorophenyl)-4-hydroxy-2-naphthoic acid, (7 grams) from Step 1, and dodecylbenzenesulfonic acid (1 gram) were added to a reaction flask containing xylene (1L) and heated to reflux and maintained at that temperature for 36 hours. The reaction was cooled and the resulting red precipitate was collected by vacuum filtration and washed with toluene. The red solid was air-dried yielding 4 grams of product. An NMR spectrum showed the product to have a structure consistent with 9-fluoro-5-hydroxy-7H-benzo[C]fluoren-7-one.

Step 3

The process of Example 1, Step 6 was followed except 9-fluoro-5-hydroxy-7H-benzo[C]fluoren-7-one from Step 2 above was used instead of 7,7-dimethyl-5-hydroxy-9-fluoro- 7H-benzo[C]fluorine. NMR analysis showed the product to have a structure consistent with 9-morpholino-5-hydroxy-7H-benzo[C]fluoren-7-one.

Step 4

The process of Example 1, Step 7 was followed except 9-morpholino-5-hydroxy-7H-benzo[C]fluoren-7-one from Step 3 above was used instead of 7,7-dimethyl-5-hydroxy-9-morpholino-7H-benzo[C]fluorine. NMR analysis showed the product to have a structure consistent with 3,3 di(4-methoxyphenyl)-11-morpholino-13-oxo-3H,13H-indeno[2',3':3,4]naphtho[1,2-b]pyran.

Step 5

The product of Step 4,3,3 di(4-methoxyphenyl)-11-morpholino-13-oxo-3H,13H-indeno[2',3':3,4]naphtho[1,2-b]pyran (2 grams) was added to a reaction flask containing tetrahydrofuran (50 mL). Under a nitrogen atmosphere at 0° C., an excess of ethyl magnesium chloride (10 mL of a 2 M solution in tetrahydrofuran) was added to the reaction flask. The resulting reaction was stirred at 0° C. for 30 minutes and then warmed to room temperature. The reaction mixture was poured onto 200 mL of ice water then acidified to pH 3 with an aqueous 2N hydrochloric acid solution. Diethylether (100 mL) was added and the organic phase separated. The solvents were removed by rotary evaporation and the resulting oil was chromatographed on a silica column using hexane:ethyl acetate (2:1) as eluant. The photochromic fractions were concentrated and the residue crystallized from methanol to give 1 gram of a white solid having a melting point of 222-225° C. An NMR spectrum showed the product to have a structure consistent with 3,3-di(4-methoxyphenyl)-13-hydroxy-13-ethyl-11-morpholino-3H,13H-indeno[2',3':3,4]naphtho[1,2-b]pyran.

EXAMPLE 5

Step 1

1,2-Dimethoxybenzene (292 grams) and a solution of benzoyl chloride (297 grams in 500 mL of methylene chloride) were added to a reaction flask under a nitrogen atmosphere. Solid anhydrous aluminum chloride (281 grams) was added portion wise to the reaction mixture occasionally cooling the reaction mixture in an ice/water bath. After the addition was completed, the reaction was stirred at room temperature for 3 hours. The reaction mixture was poured onto a 1:1 ice/1N HCl mixture (300 mL) and stirred vigorously for 15 minutes. After the different layers formed, the aqueous layer was separated and extracted into methylene chloride (100 mL) three times. The organic layers were combined and washed twice with 10 weight percent sodium hydroxide (100 mL each time), and then twice with water (100 mL each time). The solvent was removed by rotary evaporation to give a yellow solid. Recrystallization from 95% ethanol yielded 490 grams of beige needles having a melting point of 103-105° C. NMR analysis showed the product to have a structure consistent with 3,4-dimethoxybenzophenone.

Step 2

The product from Step 1, 3,4-dimethoxy benzophenone (490 grams) and diethyl succinate (354 grams) were combined in a reaction flask containing in 600 mL of toluene under a nitrogen atmosphere. The mixture was heated to 45° C. and then potassium t-butoxide (248 grams) was added portion wise over a 1-hour period. After completing the addition, the reaction mixture was heated to 45° C. and maintained at that temperature for 5 hours and then cooled to room temperature. Water (500 mL) was added to the reaction mixture and the phases separated into layers. The aqueous layer was collected and acidified to pH 2 with 4 N HCl. The resulting acidic solution was extracted five times into methylene chloride (50 mL each time). The organic extracts were combined and concentrated by rotary evaporation to provide a thick brown oil. NMR spectrum showed the desired product to have a structure consistent with 4-(3,4-dimethoxyphenyl)-4-phenyl-methoxycarbonyl-3-butenoic acid. This material was not purified further but was used directly in the next step.

Step 3

The product from Step 2 (620 grams), was added to a reaction flask containing acetic anhydride (2.1 L) under a nitrogen atmosphere and heated to reflux. The reaction mixture was maintained at the reflux temperature for 6 hours, cooled to room temperature and the solvent (acetic anhydride) was removed by rotary evaporation to give a thick gum which solidified upon standing. The solid was added to a reaction flask and dissolved in boiling methanol (3 L). After cooling overnight, the crystals (249 grams) that formed were collected by vacuum filtration, washed with methanol and air-dried. NMR spectrum showed the crystals to have a structure consistent with 1-phenyl-2-methoxycarbonyl-4-acetoxy-6,7-dimethoxy-naphthalene. The isomer 1-(3,4-dimethoxyphenyl)-2-methoxycarbonyl-4-acetoxy-naphthlene remained in the filtrate as an enriched mixture with 1-phenyl-2-methoxycarbonyl-4-acetoxy-6,7-dimethoxynaphthalene in methanol.

Step 4

The filtrate from Step 3 containing 1-(3,4-dimethoxyphenyl)-2-methoxycarbonyl-4-acetoxy-naphthalene and 5 mL of concentrated HCl were combined in a reaction flask and heated to reflux for 1 hour. The reaction was cooled and the precipitate that formed was collected by vacuum filtration washing with cold methanol yielding 27 grams of beige needles. NMR analysis showed the product to have structure consistent with 1-(3,4-dimethoxyphenyl)-2-methoxycarbonyl-4-hydroxy-naphthalene.

Step 5

Anhydrous tetrahydrofuran (100 mL) was added to a reaction flask under a nitrogen atmosphere containing 1-(3,4-dimethoxyphenyl)-2-methoxycarbonyl-4-hydroxynaphthalene (25 grams) from Step 4. The reaction mixture was cooled in an ice bath and then 264 mL of a methyl lithium solution (1.4 M in tetrahydrofuran) was added dropwise over 40 minutes. The resulting yellow reaction mixture was stirred at 0° C. for 2 hours and then slowly warmed to room temperature and stirred overnight. The reaction mixture was carefully poured onto 200 mL of an ice/water mixture. Ethyl acetate (100 mL) was added and the layers separated. The aqueous layer was collected and extracted with four 75 mL portions of ethyl acetate. The organic extracts were combined and washed with two 50 mL portions of water. The organic layer was collected, dried over anhydrous magnesium sulfate and then concentrated by rotary evaporation. The resulting oil was transferred into a reaction vessel (fitted with a Dean-Stark trap) with 500 mL of xylene and 200 mg of dodecylbenzene sulfonic acid. The reaction mixture was heated to reflux for 2 hours, cooled, and the xylene was removed by rotary evaporation. The resulting dark oil was crystallized from ethanol (95%) at reflux temperature and the resulting crystals were collected by vacuum filtration and washed with ethanol. A beige solid, 14 grams, was obtained. NMR analysis showed the product to have a structure consistent with 7,7-dimethyl-5-hydroxy-9,10-dimethoxy-7H-benzo[C]-fluorene.

Step 6

Morpholine (3.4 grams) was weighed into a dry reaction flask. Anhydrous tetrahydrofuran (50 mL) was added to the reaction flask and the resulting mixture was stirred under a nitrogen atmosphere at room temperature. Methyl lithium (25.1 mL of a 1.4 M solution in diethyl ether) was added dropwise to the reaction mixture over a 10-minute period. The temperature of the reaction mixture increased and a white solid precipitated out. 7,7-Dimethyl-5-hydroxy-9,10-dimethoxy-7H-benzo[C]-fluorene (2.5 grams) from step 5 was added over a 5-minute period to the reaction mixture. The resulting yellowish brown solution was heated overnight at reflux temperatures. After cooling to room temperature, the reaction mixture was poured into 200 mL of water. The aqueous layer was collected and 10 weight percent hydrochloric acid was added until the pH was 6. A saturated sodium chloride solution (200 mL) was added to the aqueous layer. The resulting mixture was extracted with three 200 mL portions of ethyl acetate. The organic layers were collected, combined, washed once with a saturated sodium chloride solution (300 mL) and dried over anhydrous sodium sulfate. The solvent (ethyl acetate) was removed by rotary evaporation to yield a yellowish-brown oil that foamed upon drying. This material (identified as 7,7-dimethyl-5-hydroxy-9-morpholino-10-methoxy-7H-benzo[C]-fluorene) by mass spectroscopy was not purified further but was used directly in the next step.

Step 7

7,7-Dimethyl-5-hydroxy-9-morpholino-10-methoxy-7H-benzo[C]-fluorene (1.30 grams) from Step 6, 1,1-bis(4-methoxyphenyl)-2-propyn-1-ol (1.16 grams), dodecylbenzene sulfonic acid (about 10 milligrams) and methylene chloride (200 mL) were combined in a reaction vessel and stirred at ambient temperature under a nitrogen atmosphere for 2 hours. The reaction mixture was washed twice with a saturated sodium bicarbonate solution (300 mL each time) and dried over anhydrous sodium sulfate. The solvent (methylene chloride) was removed by rotary evaporation. The resulting brown-black solid was purified by column chromatography and induced to crystallize from diethyl ether to yield 1.0 gram of a light yellow solid. NMR analysis showed the product to have a structure consistent with 3,3-di-(4-methoxyphenyl)-10-methoxy-11-morpholino-13,13-dimethyl-3H,13H-indeno[2',3':3,4]-naphtho[1,2-b]pyran.

EXAMPLE 6

The process of Example 6 was followed except that in Step 6, 1-(4-methoxyphenyl)-1-(4-morpholinophenyl)-2-propyn-1-ol (1.6 grams) was used in place of 1,1-bis(4-methoxyphenyl)-2-propyn-1-ol (1.16 grams). The resulting brown-black solid was purified by column chromatography and induced to crystallize from diethyl ether to yield 0.8 gram of a light yellow solid. NMR analysis showed the to have a structure consistent with 3-(4-methoxyphenyl)-3-(4-morpholinophenyl)-10-methoxy-11-morpholino-13,13-dimethyl-3H,13H-indeno[2',3':3,4]-naphtho[1,2-b]pyran.

EXAMPLE 7

The process of Example 1 was followed except that in Step 7, 1-(3,4-dimethoxyphenyl)-1-(4-methoxyphenyl)-2-propyn-1-ol was used instead of 1,1-di(4-methoxyphenyl)-2-propyn-1-ol to produce a solid having a melting point of 197-199° C. NMR analysis showed the product to have a structure consistent with 3-(3,4-dimethoxyphenyl)-3-(4-methoxyphenyl)-11-morpholino -13,13-dimethyl-3H,13H-indeno[2',3':3,4]naphtho[1,2-b]pyran.

EXAMPLE 8

The process of Example 1 was followed except that in Step 7, 1-(4-methoxyphenyl)-1-(4-morpholinophenyl)-2-propyn-1-ol was used instead of 1,1-di(4-methoxyphenyl)-2-propyn-1-ol. NMR analysis showed the product to have a structure consistent with 3-(4-methoxyphenyl)-3-(4-morpholinophenyl)-11-morpholino -13,13-dimethyl-3H,13H-indeno[2',3': 3,4]naphtho[1,2-b]pyran. When a portion of the recovered product was dissolved into diethylene glycol dimethyl ether and exposed to ultraviolet radiation, the solution became blue-green in color. When exposure to the ultraviolet radiation was discontinued, the solution became colorless.

Comparative Examples 1-5

Comparative Examples (CE) 1 through 5 were prepared following the procedures of U.S. Pat. Nos. 5,645,767 and 6,296,785B1. NMR analysis showed the products to have structures consistent with the following names.
CE-1—3,3-di(4-methoxyphenyl)-13,13-dimethyl-3H, 13H-indeno[2',3':3,4]naphtho[1,2-b]pyran.
CE-2—3-phenyl-3-(4-morpholino-phenyl)-13,13-dimethyl-3H,13H-indeno[2',3':3,4]naphtho-[1,2-b]pyran.
CE-3—3,3-di(4-(2-methoxyethoxyphenyl))-13,13-dimethyl-3H,13H-indeno[2',3':3,4]naphtho[1,2-b]pyran.
CE-4-3,3-di(4-methoxyphenyl)-13-hydroxy-13-ethyl-3H, 13H-indeno[2',3':3,4]naphtho[1,2-b]pyran.
CE-5 —3-(4-methoxyphenyl)-3-(4-morpholinophenyl)-13,13-dimethyl-3H,13H-indeno[2',3':3,4] naphtho[1,2-b]pyran.

EXAMPLE 9

The Indenonaphthopyran Photochromic Performance Test comprises the preparation of photochromic polymeric test samples using the Examples of the present invention and Comparative Examples in Part A and testing the photochromic performance as described in Part B.

Part A

Testing was done with the photochromic materials described in Examples 1 through 7 and Comparative Examples 1-6 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2',-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm ×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares of Part A were tested for photochromic response on an optical bench. Prior to testing on the optical bench, the photochromic test squares were exposed to 365 nm ultraviolet light for about 10 minutes at a distance of about 14 cm from the lamps to activate the photochromic compound and then placed into a 75° C. oven for 15 minutes to thermally bleach the photochromic compounds. The UVA (315 to 380 nm) irradiance at the sample was measured with a Licor Model Li-1800 spectroradiometer and found to be 22.2 Watts per square meter. The test squares were then cooled to room temperature, while exposed to fluorescent room lighting, approximately 1000 Lux for at least 2 hours and then kept covered for another 2 hours prior to testing on the optical bench.

The optical bench was fitted with an Oriel Model #66011 300 watt Xenon arc lamp, a remote controlled shutter, collimating lens, copper sulfate bath acting as a heat sink for the arc lamp, Schott WG-320 nm cut-off filter for removing short wavelength radiation; neutral density filter(s) and a sample holder. The air chamber in which testing was conducted was maintained at 72° F. or 22° C. The irradiance at the sample was measured using a Licor Model Li-1800 spectroradiometer and found to be 2.5 watts per square meter UVA (315-380 nm) and 2.78 Klux. The irradiance consistency between experiments was verified by using a GRASEBY Optronics Model S-371 portable photometer and by running a preliminary response test with a photochromic test square reference standard before samples were run.

A Sorensen, Model SRL 20-50, DC power supply controlled the Nicolas Illuminator containing a 6 volt tungsten lamp that was used as the monitoring light source for photochromic response measurements. The collimated monitoring beam of light from the tungsten lamp was passed through the sample square at a small angle (approximately 30°) normal to the square and into a Model GM-200 monochromator from Spectral Energy Corporation. The monochromator was set at the previously determined visible lambda max of the photochromic compound being tested. The light at the set wavelength was measured upon exiting the monochromator by an attached International Light research radiometer system, Model IL1700 fitted with a high gain detector, Model SHD033. LabTech Notebook data acquisition and control software version 11.0 was used to process the data and control the operation of the optical bench.

Response measurements, in terms of a change in optical density ($\Delta OD$) from the unactivated or bleached state to the activated or darkened state were determined by establishing the initial unactivated transmittance, opening the shutter from the Xenon lamp(s) and measuring the transmittance through activation at selected intervals of time, e.g., 30 seconds and 15 minutes, measuring the transmittance in the activated state, and calculating the change in optical density according to the formula: $\Delta OD = \log(\% Tb/\% Ta)$, where % Tb is the percent transmittance in the bleached state, % Ta is the percent transmittance in the activated state and the logarithm is to the base 10.

The $\Delta OD$/min., which represents the sensitivity of the photochromic compound's response to ultraviolet light, was measured after the first five (5) seconds of UV exposure, then expressed on a per minute basis. The lambda max in the ultraviolet range ($\lambda$ max (UV)) is the wavelength of the major absorption peak in the ultraviolet range closest to the visible spectrum. The lambda max in the visible light range ($\lambda$ max (Vis)) is the wavelength in the visible spectrum at which the maximum absorption of the activated form of the photochromic compound occurs. The lambda max (Visible and UV) was determined by testing the photochromic test square polymerizates of Part A in a Varian Cary 3 UV-Visible spectrophotometer.

The Fade Half Life (T ½) is the time interval in seconds for the $\Delta OD$ of the activated form of the photochromic material in the test squares to reach one half the $\Delta OD$ measured after fifteen minutes of activation at 72° F., 22° C., after removal of the source of activating light, e.g., by closing the shutter. The results of the Indenonaphthopyran Photochromic Performance Test are included in Table 1.

TABLE 1

| Example No. | λ max (UV) | λ max (Vis) | Sensitivity ΔOD/min. | ΔOD @ 30 sec. | ΔOD @ 15 min. | T ½ (seconds) |
|---|---|---|---|---|---|---|
| 1 | 395 | 604 | 0.54 | 0.26 | 1.10 | 363 |
| CE 1 | 355 | 561 | 0.33 | 0.19 | 0.78 | 129 |
| 2 | 395 | 615 | 0.54 | 0.29 | 1.65 | 736 |
| CE 2 | 355 | 583 | 0.42 | 0.21 | 1.23 | 248 |
| 3 | 395 | 602 | 0.54 | 0.29 | 1.27 | 369 |
| CE 3 | 354 | 557 | 0.39 | 0.20 | 0.78 | 133 |
| 4 | 380 | 609 | 0.43 | 0.20 | 0.55 | 48 |
| CE 4 | 360 | 562 | 0.29 | 0.12 | 0.27 | 47 |
| 5 | 391 | 603 | 0.58 | 0.29 | 1.07 | 236 |
| CE 1 | 355 | 561 | 0.33 | 0.19 | 0.78 | 129 |
| 6 | 393 | 622 | 0.58 | 0.27 | 0.98 | 167 |
| CE 5 | 356 | 589 | 0.36 | 0.17 | 0.61 | 99 |
| 7 | 363 | 604 | 0.63 | 0.31 | 1.43 | 490 |
| CE 1 | 355 | 561 | 0.33 | 0.19 | 0.78 | 129 |

Table 1 shows that each of the Example compounds demonstrates a bathochromic shift in the visible lambda max and an increase in Sensitivity when compared to the respective Comparative Example compounds in the Indenonaphthopyran Photochromic Performance Test.

The present invention has been described with reference to specific details of particular embodiments thereof. It is not intended that such details be regarded as limitations upon the scope of the invention except insofar as to the extent that they are included in the accompanying claims.

What is claimed is:

1. A naphthol represented by one of the following graphic formulae:

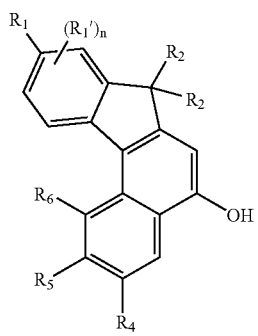

wherein
(a) R₁ is represented by:
(i) —SR₇, R₇ being chosen from $C_1$-$C_6$ alkyl, aryl, mono- or di-substituted aryl, said aryl group being phenyl or naphthyl and each of said aryl substitutents being chosen independently from $C_1$-$C_6$ alkyl, $C_1$-$C_6$ alkoxy or halogen;
(ii) —N(R₁₅)R₁₆, R₁₅ and R₁₆ each being independently chosen from hydrogen, $C_1$-$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl and said aryl group being phenyl or naphthyl;
(iii) a nitrogen containing ring represented by the following graphic formula:

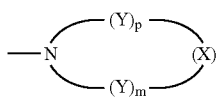

wherein each Y being independently chosen for each occurrence from —CH₂—, —CH(R₁₇)—, —C(R₁₇)(R₁₇)—, —CH(aryl)-, —C(aryl)₂- or —C(R₁₇)(aryl)-; X being —Y—, —O—, —S—, —S(O)—, —S(O₂)—, —NH—, —N(R₁₇)— or —N(aryl)-; R₁₇ being $C_1$-$C_6$ alkyl; said aryl group being phenyl or naphthyl, m being chosen from the integer 1, 2 or 3 and p being chosen from the integer 0, 1, 2 or 3; provided that when p is 0, X is Y;

(iv) a group represented by one of the following graphic formulae:

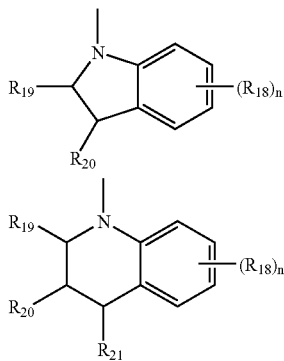

wherein each R₁₉, R₂₀ and R₂₁ being independently chosen for each occurrence in each formula from hydrogen, $C_1$-$C_5$ alkyl, phenyl or naphthyl; or the groups R₁₉ and R₂₀ together form a ring of 5 to 8 carbon atoms; R₁₈ being chosen independently for each occurrence from $C_1$-$C_6$ alkyl, $C_1$-$C_6$ alkoxy, fluoro or chloro and n being chosen from the integer 0, 1 or 2;

(v) unsubstituted, mono- or di-substituted $C_4$-$C_{18}$ spirobicyclic amine; or
(vi) unsubstituted, mono- or di-substituted $C_4$-$C_{18}$ spirotricyclic amine; said substituents for (v) and (vi) being independently chosen for each occurrence from aryl, $C_1$-$C_6$ alkyl or $C_1$-$C_6$ alkoxy or phenyl ($C_1$-$C_6$) alkyl;

(b) R₁' is independently chosen for each occurrence from $C_1$-$C_6$ alkyl or $C_1$-$C_6$ alkoxy and n being chosen from the integer 0, 1 or 2;
(c) each R₂ or each R₃ is independently chosen for each occurrence from:
(i) hydrogen, hydroxy, amino, mono- or di-substituted amino, $C_1$-$C_{12}$ alkyl, $C_3$-$C_{12}$ alkylidene, $C_2$-$C_{12}$ alkylidyne, vinyl, $C_3$-$C_7$ cycloalkyl, $C_1$-$C_6$ aloalkyl, allyl, benzyl, mono-substituted benzyl, chloro, fluoro or —C(O)W, wherein W being hydroxy, $C_1$-$C_6$ alkyl, $C_1$-$C_6$ alkoxy, phenyl, mono-substituted phenyl, amino, mono($C_1$-$C_6$)alkylamino, di($C_1$-$C_6$)alkylamino, morpholino, piperidino or pyrrolidyl; said amino substituents being $C_1$-$C_6$ alkyl, phenyl, benzyl or naphthyl; each of said benzyl and phenyl substituents being $C_1$-$C_6$ alkyl or $C_1$-$C_6$ alkoxy;
(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (c) (ii) being chosen independently for each occurrence from chloro, fluoro, $C_1$-$C_6$ alkyl or $C_1$-$C_6$ alkoxy;
(iii) a monosubstituted phenyl, said phenyl having a substituent located at the para position being —(CH₂)$_t$— or —O—(CH₂)$_t$—, connected to an aryl group which is a member of another photochromic material, and t being chosen from the integer 1, 2, 3, 4, 5 or 6;
(iv) —OR₈, R₈ being chosen from $C_1$-$C_6$ alkyl, $C_1$-$C_6$ acyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$) alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, tri($C_1$-$C_6$)alkylsilyl, tri($C_1$-$C_6$)alkoxysilyl, di($C_1$-$C_6$)alkyl ($C_1$-$C_6$)alkoxysilyl, di($C_1$-$C_6$)alkoxy($C_1$-$C_6$)alkylsilyl, benzoyl, monosubstituted benzoyl, naphthoyl or mono-substituted naphthoyl; each of said benzoyl and naphthoyl substituents being independently chosen from $C_1$-$C_6$ alkyl or $C_1$-$C_6$ alkoxy; or R₈ being —CH(R₉)Q, wherein R₉ being chosen from hydrogen or $C_1$-$C_3$ alkyl and Q being chosen from —CN, —CF₃, or —COOR₁₀ and R₁₀ being chosen from hydrogen or $C_1$-$C_3$ alkyl; or R₈ being —C(O)V, wherein V being chosen from hydrogen, $C_1$-$C_6$ alkoxy, phenoxy, mono- or di-($C_1$-$C_6$)alkyl substituted phenoxy, mono- or di-($C_1$-$C_6$)alkoxy substituted phenoxy, an unsubstituted, mono- or di-substituted aryl group, phenyl or naphthyl, amino, mono($C_1$-$C_6$)alkylamino, di($C_1$-$C_6$) alkylamino, phenylamino, mono- or di-($C_1$-$C_6$)alkyl substituted phenylamino, or mono- or di-($C_1$-$C_6$) alkoxy substituted phenylamino; each of said aryl group substituents being independently chosen from $C_1$-$C_6$ alkyl or $C_1$-$C_6$ alkoxy;
(v) —CH(Q')₂, Q' being chosen from —CN or —COOR₁₁ and R₁₁ being chosen from hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl or an unsubstituted, mono- or di-substituted aryl group, phenyl or naphthyl; each of said aryl group substituents being independently chosen from $C_1$-$C_6$ alkyl or $C_1$-$C_6$ alkoxy;
(vi) —CH(R₁₂)G, R₁₂ being chosen from hydrogen, $C_1$-$C_6$ alkyl or an unsubstituted, mono- or di-substituted aryl group, phenyl or naphthyl, and G being chosen from —COOR$_{11}$, —COR$_{13}$ or —CH$_2$OR$_{14}$, wherein R$_{13}$ being chosen from hydrogen, C$_1$-C$_6$ alkyl, an unsubstituted, mono- or di-substituted aryl group, phenyl or naphthyl, amino, mono(C$_1$-C$_6$)alkylamino, di(C$_1$-C$_6$)alkylamino, phenylamino, mono- or di-(C$_1$-C$_6$)alkyl substituted phenylamino, mono- or di-(C$_1$-C$_6$)alkoxy substituted phenylamino, diphenylamino, mono- or di(C$_1$-C$_6$)alkyl substituted diphenylamino, mono- or di(C$_1$-C$_6$)alkoxy substituted diphenylamino, morpholino or piperidino R$_{14}$ being chosen from hydrogen, —C(O)R$_{11}$, C$_1$-C$_6$ alkyl, C$_1$-C$_3$ alkoxy(C$_1$-C$_6$)alkyl, phenyl(C$_1$-C$_3$)alkyl, mono(C$_1$-C$_6$)alkoxy substituted phenyl(C$_1$-C$_3$)alkyl or an unsubstituted, mono- or di-substituted aryl group, phenyl or naphthyl, each of said aryl group substituents being independently chosen from C$_1$-C$_6$ alkyl or C$_1$-C$_6$ alkoxy;

(vii) the group T represented by the formula:

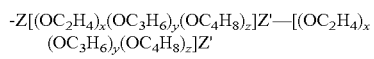

wherein -Z being chosen from —C(O)— or —CH$_2$—, Z' being chosen from C$_1$-C$_3$ alkoxy or a polymerizable group, x, y and z each being independently chosen from a number between 0 and 50, and the sum of x, y and z being between 2 and 50; or (viii) R$_2$ and R$_2$ or R$_3$ and R$_3$ together form an oxo group;

(d) R$_4$ is chosen from hydrogen, C$_1$-C$_6$ alkyl or the group R$_a$ chosen from:

(i) —OR$_8$', R$_8$' being chosen from phenyl(C$_1$-C$_3$)alkyl, C$_1$-C$_6$ alkyl, mono(C$_1$-C$_6$)alkyl substituted phenyl (C$_1$-C$_3$)alkyl, mono(C$_1$-C$_6$)alkoxy substituted phenyl (C$_1$-C$_3$)alkyl, C$_1$-C$_6$ alkoxy(C$_2$-C$_4$)alkyl, C$_3$-C$_7$ cycloalkyl, mono(C$_1$-C$_4$)alkyl substituted C$_3$-C$_7$ cycloalkyl, C$_1$-C$_6$ chloroalkyl, C$_1$-C$_6$ fluoroalkyl, allyl or —CH(R$_9$)Q, R$_9$ being chosen from hydrogen or C$_1$-C$_3$ alkyl; or (ii) a group chosen from:

(1) —N(R$_{15}$)R$_{16}$ wherein R$_{15}$ and R$_{16}$ being the same as described hereinbefore in (a) (ii);

(2) a nitrogen containing ring represented by the following graphic formula:

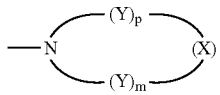

wherein Y, X, m and p being the same as described hereinbefore in (a) (iii); or (3) a group represented by the following graphic formulae:

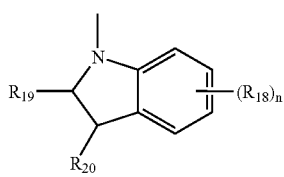

-continued

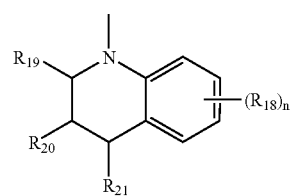

wherein R$_{18}$, R$_{19}$, R$_{20}$, R$_{21}$ and n being the same as described herein before;

(e) R$_5$ is chosen from hydrogen, C$_1$-C$_6$ alkyl or R$_a$, said R$_a$ being the same as described hereinbefore in (d);

(f) R$_6$ is chosen from hydrogen, C$_1$-C$_6$ alkyl or R$_a$, said R$_a$ being the same as described hereinbefore in (d); or (g) R$_5$ and R$_6$ together form one of the following graphic formulae:

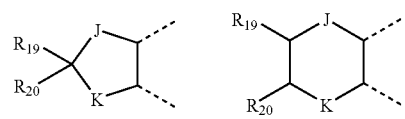

wherein J and K being independently chosen for each occurrence in each formula from oxygen or —N(R$_{15}$)—, R$_{15}$ being the same as described hereinbefore in (a) (ii), R$_{19}$ and R$_{20}$ each being the same as described hereinbefore in (a) (iv).

2. The naphthol of claim 1 wherein said naphthol is represented by one of the following graphic formulae:

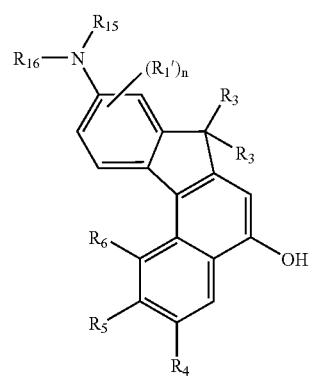

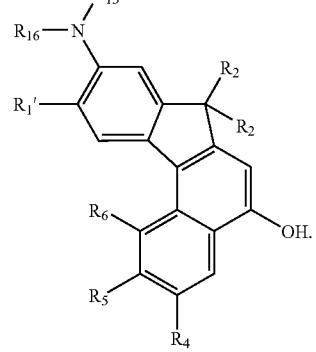

3. The naphthol of claim 1 wherein said naphthol is chosen from:
- (a) 7,7-dimethyl-5-hydroxy-9-morpholino-7H-benzo[C]fluorene;
- (b) 7,7-dimethyl-5-hydroxy-10-methoxy-9-morpholino-7H-benzo[C]fluorene;
- (c) 7-dimethyl-7-methoxy-5-hydroxy-9-dimethylamino-7H-benzo[C]fluorene;
- (d) 7-ethyl-7-methoxy-5-hydroxy-9-piperidino-7H-benzo[C]fluorene;
- (e) 7,7-dimethyl-5-hydroxy-9-piperidino-7H-benzo[C]fluorene;
- (f) 7,7-dimethyl-3-methoxy-5-hydroxy-9-morpholino-7H-benzo[C]fluorene;
- (g) 7,7-dimethyl-3,4-dimethoxy-5-hydroxy-9-morpholino-7H-benzo[C]fluorene;
- (h) 7,7-dimethyl-3-methoxy-4-methyl-5-hydroxy-9-morpholino-7H-benzo[C]fluorene;
- (i) 7,7-dimethyl-5-hydroxy-9-phenylthio-7H-benzo[C]fluorene;
- (j) 7-phenyl-7-hydroxy-3-methoxy-4-methyl-5-hydroxy-9-morpholino-7H-benzo[C]fluorene;
- (k) 7-ethyl-7-methoxy-5-hydroxy-9-phenylthio-7H-benzo[C]fluorene; or
- (l) mixtures thereof. Fixed

* * * * *